United States Patent [19]
Volk

[11] Patent Number: 5,430,506
[45] Date of Patent: * Jul. 4, 1995

[54] INDIRECT OPHTHALMOSCOPY LENS FOR USE WITH SLIT LAMP BIOMICROSCOPE

[76] Inventor: Donald A. Volk, 7893 Enterprise Dr., Mentor, Ohio 44060

[*] Notice: The portion of the term of this patent subsequent to Jul. 26, 2011 has been disclaimed.

[21] Appl. No.: 131,086

[22] Filed: Oct. 1, 1993

Related U.S. Application Data

[63] Continuation-in-part of Ser. No. 973,988, Nov. 6, 1992, Pat. No. 5,333,017.

[51] Int. Cl.$^6$ ............................................. A61B 3/10
[52] U.S. Cl. ................................... 351/205; 359/708
[58] Field of Search ................. 359/708, 712; 351/205

[56] References Cited

U.S. PATENT DOCUMENTS 3,944,341 3/1976 Pomerantzeff ........................ 351/7
5,046,836 9/1991 Vok .................................... 351/219

OTHER PUBLICATIONS

U.S. patent application Ser. No. 07/973,988, D. Volk, filed Nov. 6, 1992 U.S. Pat. No. 5,333,017, Patented Jul. 26, 1994.

Primary Examiner—Loha Ben
Assistant Examiner—Thomas Robbins
Attorney, Agent, or Firm—Oldham, Oldham & Wilson Co.

[57] ABSTRACT

The lens of the invention is specifically designed for use with a slit lamp biomicroscope or operating microscope in the examination or treatment of a patient's eye. The invention consists of one or more coaxial lens elements, with at least one of the lens elements utilizing at least one convex aspheric surface of revolution. The aspheric surface or surfaces utilized are chosen to correct astigmatic imagery of the lens, with the formed aerial image free of excessive field curvature and astigmatism. The lens is held at a distance from the patient's eye pupil corresponding to the secondary focal length of the lens. If the examined eye is emmetropic, and the lens is held in a position wherein the entrance pupil of the lens is conjugate with that of the examined eye, an image of the entrance pupil of the patient's eye will be formed at the pupil aperture of the optical system of the slit lamp biomicroscope used to observe the aerial image of the fundus as produced by the lens. The ratio of the apical radii of curvature of each surface and the ratio of the apical eccentricities of each surface are chosen to optimally correct for astigmatic imagery as well as pupil imagery of the lens, being dependent upon the index of refraction of the optical quality glass or plastic used in the production of such lenses. The indirect ophthalmoscopy lens of the invention therefore provides a sharper, focused fundus image and extremely wide field of view by optimally correcting for the primary image quality of the lens, as determined by astigmatism and image flatness, as well as the spherical aberration of the conjugate pupil image, specific to the pupil of the objective lens system of the observing slit lamp or other biomicroscope.

34 Claims, 11 Drawing Sheets

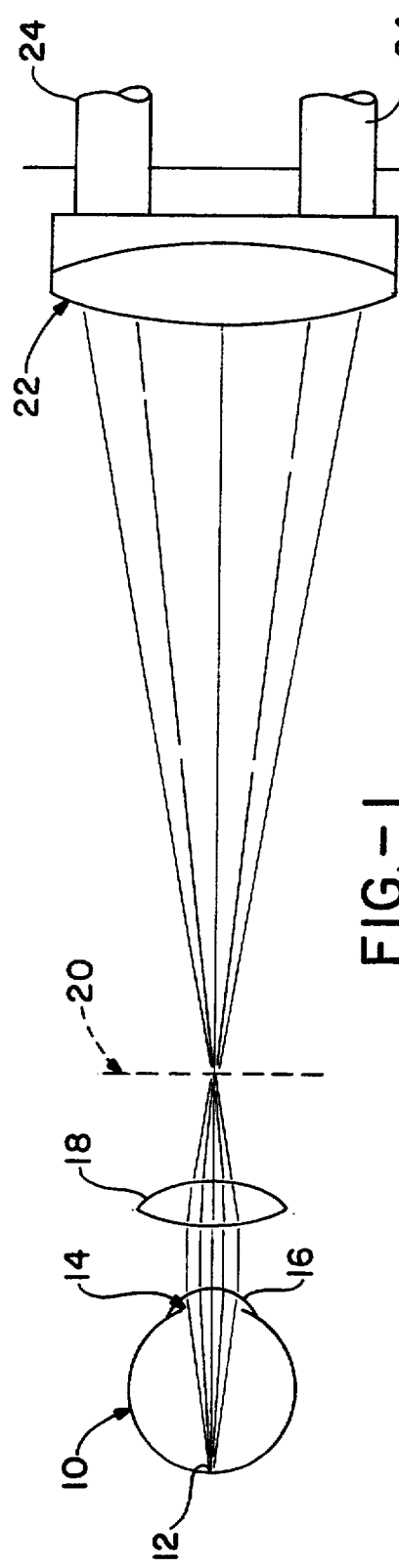
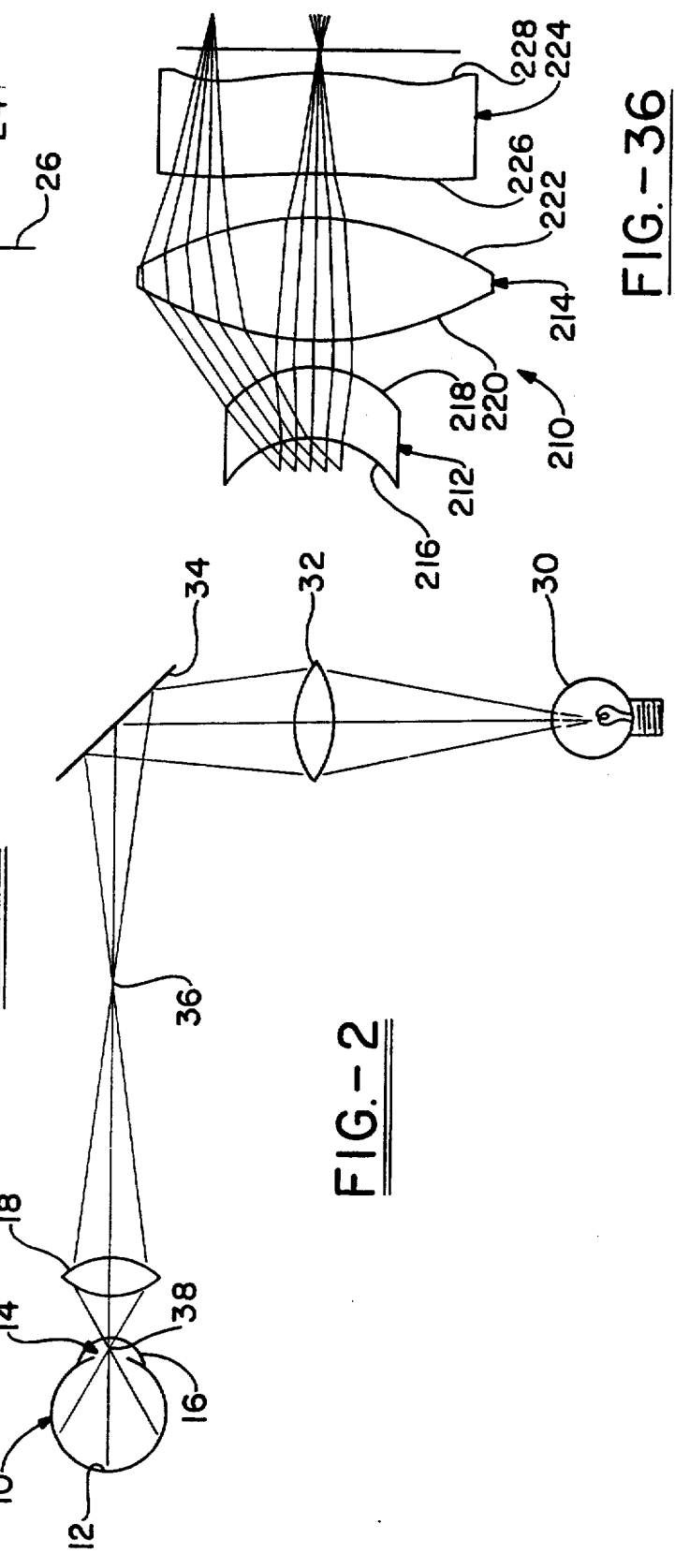

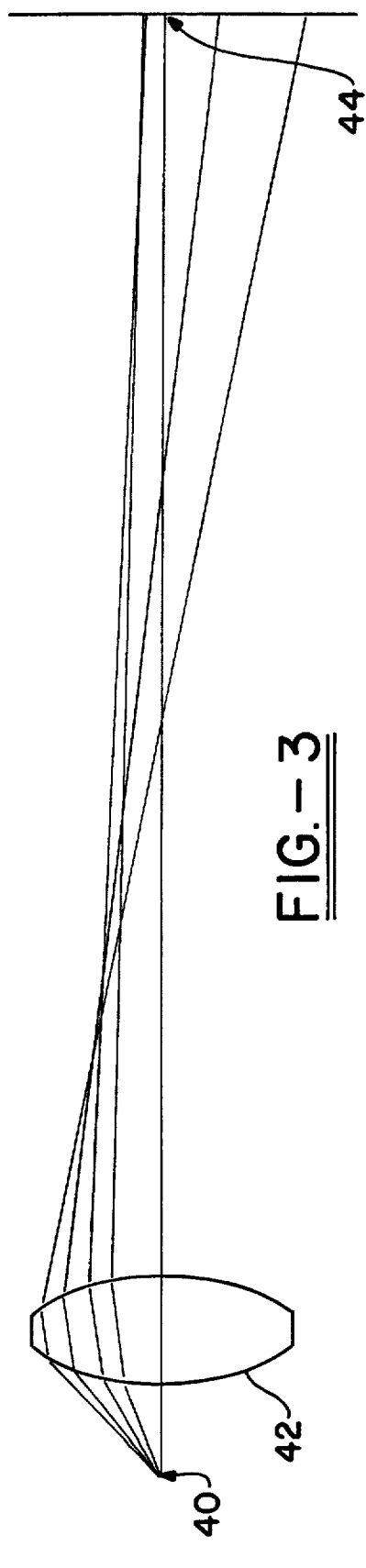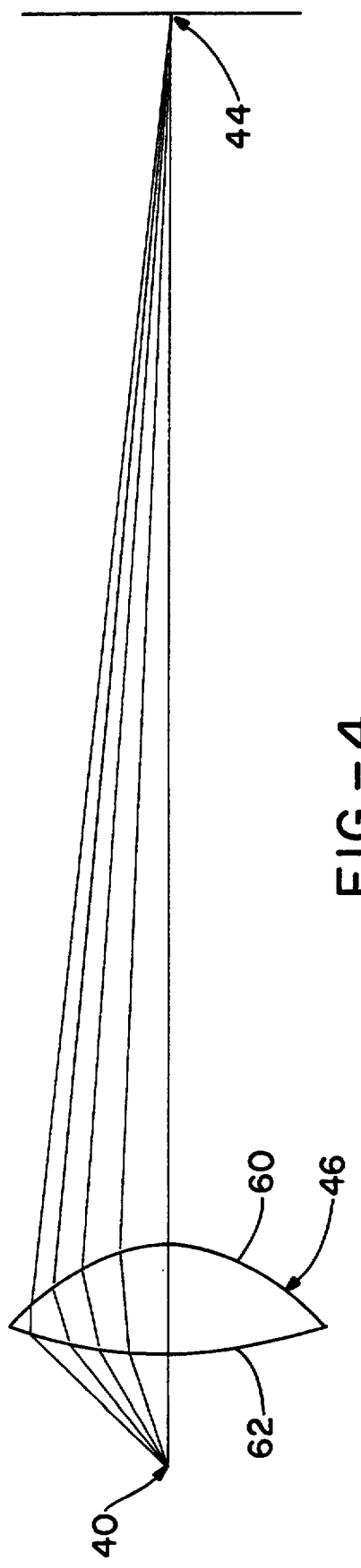

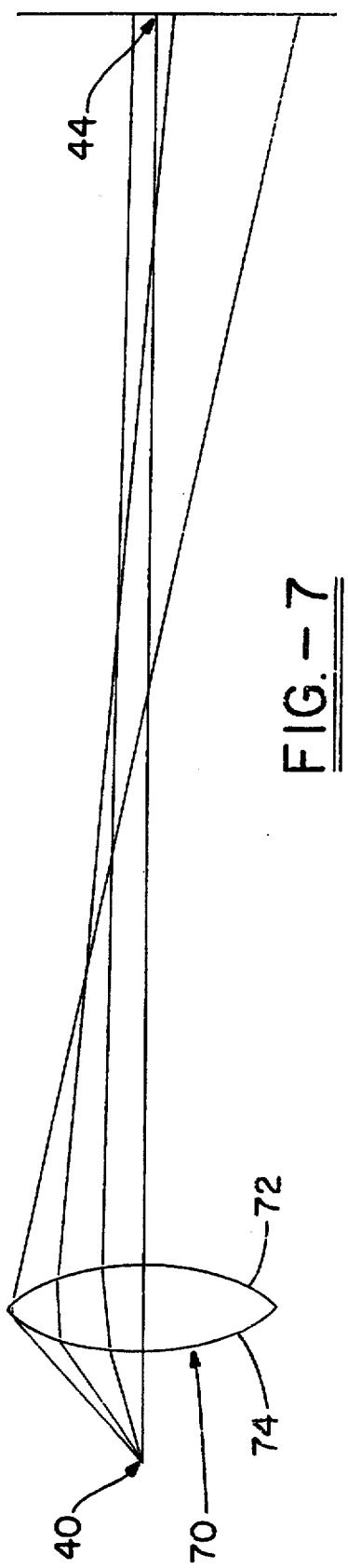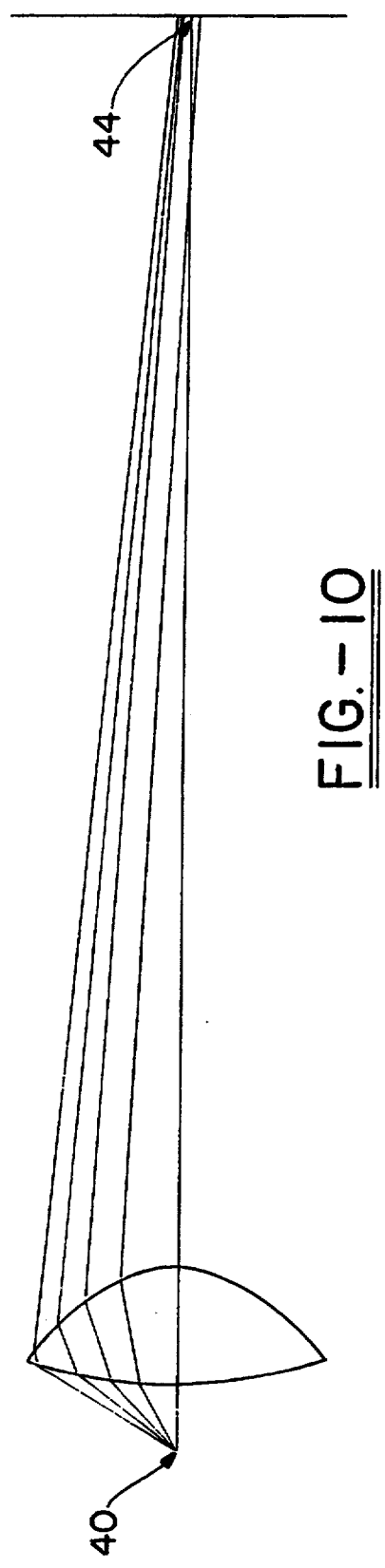

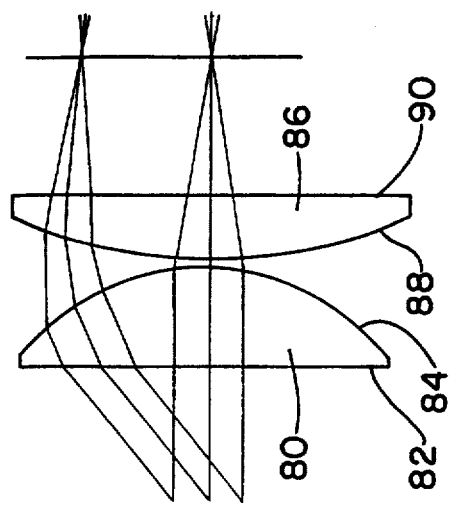
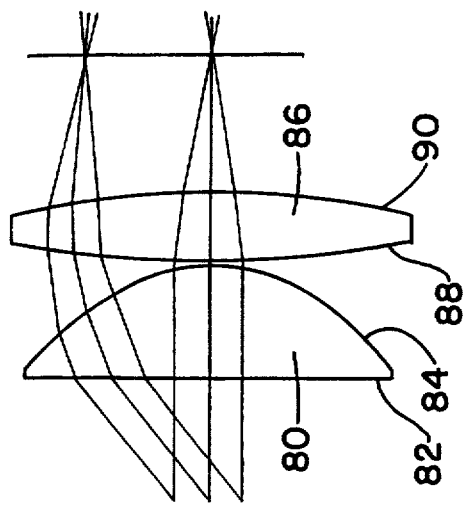
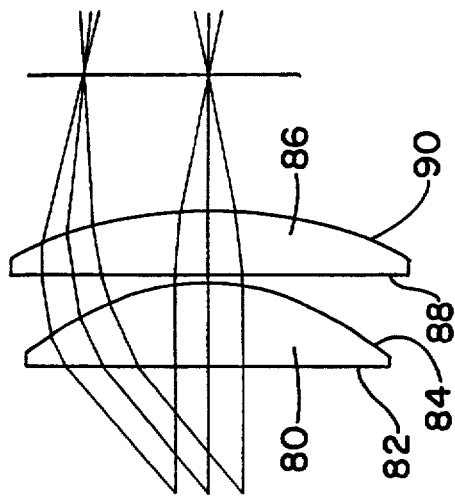
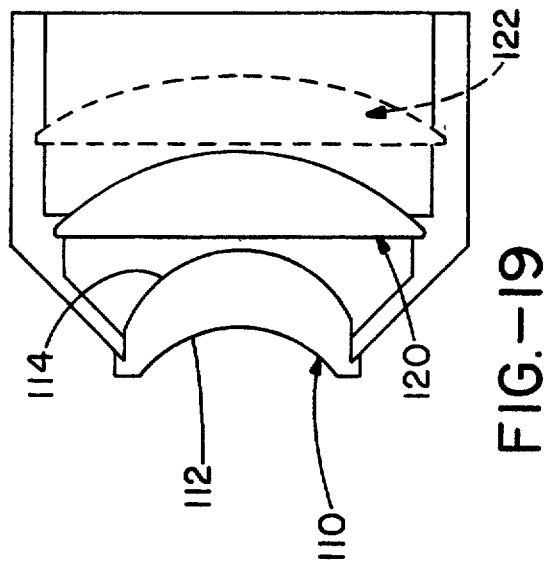
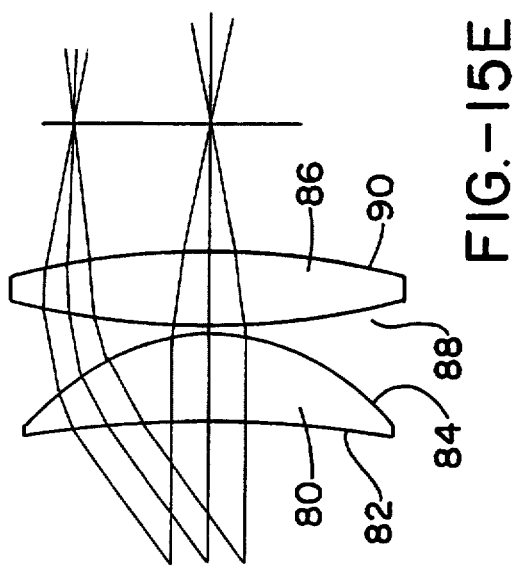
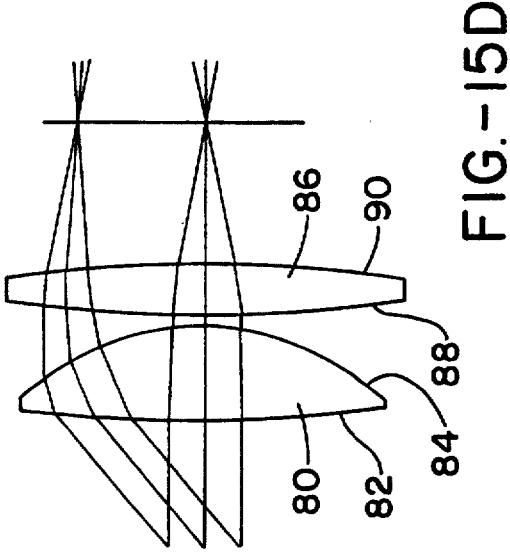

INDIRECT OPHTHALMOSCOPY LENS FOR USE WITH SLIT LAMP BIOMICROSCOPE

TECHNICAL FIELD

This application is a Continuation-In-Part of the U.S. application Ser. No. 07/973,988, filed Nov. 6, 1992, now U.S. Pat. No. 5,333,017.

This invention relates generally to in an indirect ophthalmoscopy lens system or adapter lens system for use with an indirect ophthalmoscopy lens, which is specifically designed for examination or treatment of the fundus of the eye by means of a slit lamp biomicroscope or other operating microscope. The optical lens functions both as a condensing lens for converging light from the slit lamp biomicroscope light source into the eye to illuminate the fundus of the eye, and as an image-forming lens adapted to form an aerial image of the fundus of the eye which is viewed with the biomicroscope or other observing optical system. More particularly, the invention relates to an improved indirect ophthalmoscopy lens system or adapter lens system for use with an indirect ophthalmoscopy lens, the lens system providing an extremely wide field of view and better image resolution, particularly at the peripheral regions of the formed image. The lens is particularly adapted for use with the slit lamp microscope, wherein the quality of the imagery of the eye pupil of the examined eye conjugate with the slit lamp biomicroscope "pupil" is optimized along with correction of primary image quality. In this manner, the image-forming qualities of the lens remain optimized while the viewability of the formed image using the binocular microscope of the slit lamp or other instrument is enhanced.

BACKGROUND OF THE INVENTION

Indirect ophthalmoscopy techniques are now in widespread use in diagnostic and therapeutic procedures in the field of ophthalmology. Indirect ophthalmoscopy techniques include the use of a hand-held lens, in conjunction with a binocular indirect ophthalmoscope, and more recently in biomicroscopic examination or treatment of the fundus using a slit lamp biomicroscope or operating microscope. The so-called hand-held condensing lens used in indirect ophthalmoscopy performs two functions: condensing the light from the source toward the entrance pupil of the eye, thereby illuminating the fundus, and forming an inverted real aerial image of the fundus at approximately the from focal distance of the lens. It has been found that indirect ophthalmoscopy is superior to direct ophthalmoscopy in the examination of retinopathies, retinal separation, retinal tumors, intraocular foreign bodies, and further in the ability to see fundus lesions which may not be viewable if there are opacities of the ocular media. The hand-held lenses used in indirect ophthalmoscopy have been of a variety of types, with each affording some advantages in the examination of the fundus.

The first hand-held indirect ophthalmoscopy lens which was used as a condensing and image-forming lens, included convex spherical surfaces and was of low power. The aerial image produced with such a spherical lens is magnified and inverted, but was considerably blurred, particularly toward the periphery of the formed image. A two element Ramsden style indirect ophthalmoscopy lens was thereafter produced by Rodenstock. This lens design incorporates spherical convex surfaces, and is capable of improved optical quality over that of a single element plano-convex or bi-convex lens, but the limited benefits of such a design are outweighed by increased surface reflections and light loss. Subsequently, improvements were noted by the use of slightly higher powered single element lenses, each having one aspheric surface with the other surface being plano or spherical. Although the use of a single aspherical surface in the indirect ophthalmoscopy lenses does show great improvement over spherical indirect ophthalmoscopy lenses, lens aberrations may remain such that light from the illumination source is not converged to a focus at the entrance pupil of the eye, and the formed aerial image of the fundus may show aberrations and increasing astigmatic effects particularly in the peripheral regions. These designs have been subsequently improved upon with the use of two aspherical surfaces incorporated into the indirect ophthalmoscopy lens. The first use of a double aspheric indirect ophthalmoscopy lens, designed for use with the indirect ophthalmoscope was described in U.S. Pat. No. 4,738,521, by David Volk, wherein a lens for use in indirect ophthalmoscopy incorporates both the front and back surfaces of the lens being aspheric surfaces of revolution of conoid type. This double aspheric lens design substantially improved the quality of the formed aerial image by reducing aberrations including field curvature, astigmatism, and distortion. The use of double aspheric lenses, wherein the surfaces are particularly conoid surfaces, has been found to be of distinct advantage in indirect ophthalmoscopy and has made possible the use of much stronger lenses while providing increased clarity of the image with increased size of the field of view.

In the Jun. 1982 edition of Ophthalmology Times, there was reported the use of a "periscopic lens" for use in slit lamp fundoscopy. This double plano-convex lens system was similar to the Ramsden style indirect ophthalmoscopy lens produced by Rodenstock but of smaller diameter and higher power. In that spherical surfaces were utilized, only limited improvement in optical quality could be realized, with the remaining inherent problems of reduced field as well as reflection and light loss as seen in the Rodenstock lens.

More recently, there has been developed a symmetrical double aspheric indirect ophthalmoscopy lens particularly suited for use with the slit lamp biomicroscope. This lens is described in U.S. Pat. No. 4,627,694, also by David Volk. The symmetrical non-conoid double aspheric lenses as shown in this patent are of small diameter, with the aspheric surfaces described as having decreasing curvature from the apices of the surfaces peripheralward, providing improved correction of aberrations including field curvature, astigmatism, and distortion. Lenses made according to this design have demonstrated themselves to be better suited for use with the slit lamp biomicroscope and have yielded significant improvement in the examiner's ability to see details in the aerial image of the fundus, yet this lens design, like the periscopic lens and its predecessor the El Bayadi lens, does not account for pupil aberrations, which may be inherent in the lens design and which degrade the optical and performance characteristics of a lens, especially as it relates to observation of the fundus image using the slit lamp biomicroscope. Similarly, other prior indirect ophthalmoscopy lenses have apparently neglected completely the effects of pupil aberration in their design.

Particular problems arise when attempting to use a slit lamp biomicroscope for viewing of the aerial image formed by an indirect ophthalmoscopy lens. If the lens is of lower power, the beam of light from the slit lamp light source associated with the biomicroscope cannot be enlarged sufficiently to fill the full aperture of the lens, leaving a considerable portion of the lens unused in its condensing function. Additionally, the longer focal length, lower power lenses pose the problem of requiring positioning of the biomicroscope at a location which exceeds the range of travel built into the instrument. With the development of the double aspheric indirect ophthalmoscopy lenses described above, these problems were overcome by enabling the use of higher powered lenses, allowing greater illumination of the fundus, increased field of view, and a shorter working distance well within the range of adjustment of the slit lamp biomicroscope. Although such lens design improvements have played an important role in present day eye fundus diagnostic and therapeutic techniques, especially with respect to diagnosis of diseases of the vitreous and retina, there has not been developed an indirect ophthalmoscopy lens particularly designed for use with a slit lamp biomicroscope, which optimally corrects for pupil aberrations as well as the more commonly considered aberrations of field curvature, astigmatism, and distortion.

An indirect ophthalmoscopy lens for use with a slit lamp biomicroscope must also be positioned relative to the patient's eye, such that the conjugate focus of the slit lamp light source through the lens is at approximately the center of the entrance pupil of the patient's eye. The lens must thus be positioned a sufficient distance from the entrance pupil to form the conjugate focus of the slit lamp light source at the proper position for greatest illumination of the fundus. For higher powered lenses, the lens is positioned relatively close to the front of the patient's cornea, while the microscope of the slit lamp is positioned at a significant distance from the patient in order to allow observation of the formed aerial image of the fundus. The distance from the aerial image to the biomicroscope apparatus is dependent upon the attributes of the slit lamp microscope and particularly the focal distance of the objective lens system of the microscope. For the purpose of providing a wider field of view of the fundus by means of slit lamp ophthalmoscopy, the particular diameters of the more highly powered prior art lenses have been made relatively large, such that light rays originating at the more peripheral portions of the illuminated fundus, proceeding through the pupil and cornea, are incident upon the posterior lens surface at its periphery. Although refracted through the lens and contributing to the aerial image formation, these peripheral rays, as a result of inadequate lens design, in fact do not provide peripheral fundus imagery to the practitioner viewing through the slit lamp biomicroscope. This is due to the pupil aberrations of the indirect ophthalmoscopy lens, and the fact that the lens design has not addressed the optical characteristics and requirements of the slit lamp biomicroscope itself. It is therefore seen that the field of view and the image quality obtainable by prior art indirect ophthalmoscopy lenses has not been optimized for examination using a slit lamp microscope, the quality of the imagery of the eye pupil as it specifically relates to the slit lamp microscope pupil having been completely neglected. An indirect ophthalmoscopy lens with significant pupil aberration causes excess vignetting of light rays, even at the mid-peripheral portions of the field of view. In certain cases, the rays from the edge of the field of view may completely miss the objective of the slit lamp microscope. While the hand-held indirect ophthalmoscopy lens is positioned in front of the patient's eye such that the focus of the slit lamp illumination is at or near the center of the pupil of the patient's eye, the lens, remaining in the same location, must also collect rays exiting the patient's eye, and fulfilling its optical functions, provide the maximum obtainable field of view, clear and sharp fundus imagery, and direct the chief rays of such bundles of light to the biomicroscope pupil. Without these aspects of the lens considered in its design, compromised performance will certainly result.

SUMMARY OF THE INVENTION

Based upon the foregoing, there has been found a need to provide a hand-held indirect ophthalmoscopy lens or lens system, wherein the condensing and image-forming functions, as well as the pupil characteristics of the lens are optimized for examination using the slit lamp biomicroscope or other operating microscope.

The lens or adapter lenses of the invention are designed for use with a slit lamp biomicroscope in the examination of a patient's eye. One or more lens elements may comprise the indirect ophthalmoscopy lens system or adapter lens system of this invention. In a first embodiment, a single bi-convex lens has first and second aspheric surfaces which are coaxial and non-symmetrical with respect to one another. The magnitude and shape of each of the first and second aspheric surfaces is defined by the polynomial:

$$y=(2rx+(e^2-1)x^2)^{\frac{1}{2}}+Ax^F+Bx^G+Cx^H;$$

where r equals the apical radius of curvature of each surface, e equals the apical eccentricity of each surface, and co-efficients A, B, and C equal successive terms in the polynomial, and F, G, and H equal exponents in the successive terms. The aspheric surfaces are chosen to correct astigmatic imagery of the lens, with the formed aerial image substantially free of excessive field curvature and astigmatism. In an alternative embodiment directed to a compound lens configuration, the lens may comprise two or more lens elements with at least one of the surfaces of one of the lens elements being an aspheric surface of revolution. Again, the at least one aspheric surface is chosen to correct astigmatic imagery of the lens with the compound lens forming an aerial image of the fundus of the eye which is substantially free of excessive field curvature and astigmatism. In each embodiment of the indirect ophthalmoscopy lens, the lens is adapted to be hand held, and in the preferred embodiment includes a supporting housing which enables the lens to be held at a distance from the patient's eye pupil corresponding to the back focal length of the lens. If the examined eye is emmetropic, and the lens is held in a position wherein the entrance pupil of the lens is conjugate with that of the examined eye, an image of the entrance pupil of the patient's eye will be formed at the pupil aperture of the optical system of the slit lamp biomicroscope used to observe the aerial image of the fundus as produced by the lens. The lens of the invention provides wide-angle viewing of the interior of the human eye, with imagery of the lens being well corrected for both the quality of the formed aerial image as well as quality of the pupil imagery of the lens. The pupil imagery of the lens refers to the degree to which the lens is corrected for spherical aberrations of the pupil. If the pupil imagery is poor, light rays from the outer extremes of the wide-angle view will only partially fall into the pupil of the slit lamp biomicroscope used for viewing the aerial image. In a worst case scenario, bad pupil imagery prevents extreme field points from being seen at all, as all the rays completely miss the slit lamp biomicroscopy pupil. Spherical aberration of the pupil is found to increase with at least the cube of the field angle, and large amounts of pupil aberration can therefore be present which will adversely affect examination of the eye using a slit lamp biomicroscope. In a first embodiment, the ratio of the apical radii of curvature of each surface and the ratio of the apical eccentricities of each surface are chosen to optimally correct for astigmatic imagery as well as pupil imagery of the lens. In an alternative embodiment, a compound lens may include at least one aspheric surface, the design of which allows optimization of aerial image quality as well as pupil image quality. In the compound lens design, the other surfaces of each lens in the system may be concave, convex, or plano.

As another alternative embodiment, an adapter lens system is designed for use with an indirect ophthalmoscopy lens system of one or more lenses, having a predetermined power useful in certain diagnostic or treatment procedures. In conjunction with such a lens, the adapter lenses provide a plurality of attachments which make it possible to change the net power or optical characteristics of the indirect ophthalmoscopy lens while simultaneously retaining both the good retinal imagery as well as good pupil imagery. Such adapter lenses may be of both contact and non-contact types and be of both plus and minus power. The adapter lens system may comprise one or more lenses including simple plano-convex, simple planoconcave, bi-convex and bi-concave surfaces. The adapter lens system includes a housing which is easily fitted into a housing associated with an indirect ophthalmoscopy lens system on either or both sides of the indirect ophthalmoscopy lens.

The indirect ophthalmoscopy lens and adapter lenses of the invention provide a clear and sharply focused fundus image and extremely wide field of view by optimally correcting for the primary image quality of the lens, as determined by astigmatism and image flatness, as well as the spherical aberration of the cojugate pupil image, specific to the pupil of the objective lens system of the observing slit lamp biomicroscope.

BRIEF DESCRIPTION OF THE DRAWINGS

A better understanding of the invention will be obtained upon a further reading of the detailed description in conjunction with the drawings, wherein:

FIG. 1 is a schematic diagram of the observation optical system of a typical slit lamp biomicroscope;

FIG. 2 is a schematic illustration of the illumination system used in a typical slit lamp biomicroscope;

FIG. 3 shows the pupil imagery of a prior an indirect ophthalmoscopy lens;

FIG. 4 shows the pupil imagery of an indirect ophthalmoscopy lens in accordance with the invention;

FIG. 7 shows the pupil imagery of another prior art indirect ophthalmoscopy lens;

FIG. 10 shows the pupil imagery of another example of an indirect ophthalmoscopy lens in accordance with the invention;

FIGS. 15a–15e show alternate embodiments of the indirect ophthalmoscopy lens of the invention, incorporating a compound lens design;

FIG. 19 shows an ophthalmoscopic contact lens in accordance with the invention;

FIG. 36 shows another embodiment of an adapter lens system of the invention.

DETAILED DESCRIPTION OF THE INVENTION

Figure 8:
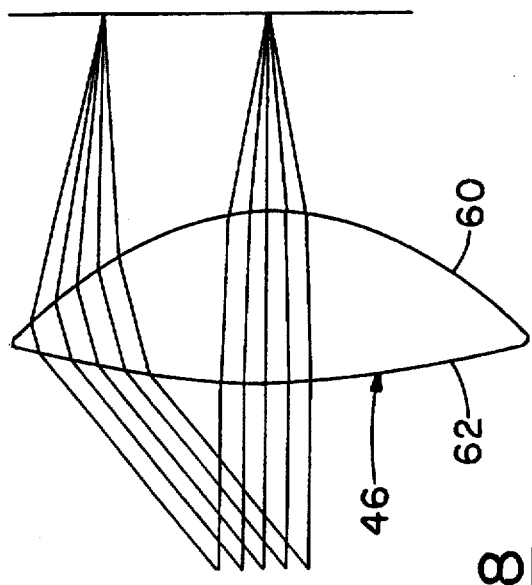
FIG. 8 shows a schematic representation of tangential ray imaging characteristics for the indirect ophthalmoscopy lens in accordance with the invention.

Turning now to FIG. 1, there is shown the light ray pathways of a binocular indirect ophthalmoscopy optical system for a typical slit lamp biomicroscope, wherein light from the fundus 12 of an examined eye 10 emanates from the fundus 12 through the pupil 14 of the eye 10 to proceed through the cornea 16 and to the observation optical system of the biomicroscope. Generally, indirect ophthalmoscopy with the slit lamp biomicroscope is performed with the pupil 14 of the examined eye 10 dilated, thus permitting the greatest illumination and therefore widest field of view of the fundus 12. Dilation of the pupil 14 will also facilitate binocular stereoscopic viewing of the aerial image of the fundus 14 with the slit lamp biomicroscope. Light rays emerging from points on fundus 12 are directed to an indirect ophthalmoscopy lens 18, which acts to converge the light toward an image plane 20, where it is intended that a sharp, clear, aberration-free image of the fundus will be formed. When examining an emmetropic eye, the position of image plane 20 should coincide with the anterior focus of the indirect ophthalmoscopy lens 18 as well as the parfocal plane of the slit lamp illumination beam and microscope objectives. As seen in FIG. 1, light rays emanating from the fundus 12 will continue past image plane 20 and toward the slit lamp front objective lenses 22 of a typical slit lamp microscope. The objective lenses 22 of the slit lamp microscope direct light from the indirect ophthalmoscopy lens 18 to a pair of eye pieces or separate ocular optical systems at 24 for binocular and stereoscopic viewing of the fundus image formed at plane 20. An objective diaphragm 26 limits light rays entering the eye pieces of the slit lamp microscope, and provides the aperture of the observation optical system. Although not distinctly shown in FIG. 1, the viewing system of the slit lamp microscope may also include in each of the binocular viewing optical systems, a Galilean telescope system, further objective lenses, reflecting prisms or mirrors as well as eye piece oculars and associated field of vision diaphragms. Although the construction of slit lamp microscopes varies to some degree, each will include an objective lens system 22 for focusing light emerging from the indirect ophthalmoscopy lens 18 toward the individual eye pieces 24 of the microscope. The objective lens system 22 will define the "pupil" of the slit lamp microscope corresponding to the back focus of the optical system. Although there is shown in FIG. 1 the formation of a single aerial image of the fundus which is an object for the objective lens of the biomicroscope, with binocular viewing capabilities, there are two overlapping slightly laterally displaced and slightly different aerial images which are viewed with the respective eyes of the examiner binocularly through the corresponding optics of the biomicroscope. As is well known, the two images as seen with the eyes of the examiner creates the retinal image disparity required for stereopsis.

In FIG. 2, the illumination system of a typical slit lamp microscope is also shown, which includes a light source 30 for generating illuminating light which is directed to a condenser lens 32. The light from light source 30 is converged via lens 32 toward a reflecting surface 34, such as a mirror, and reflected toward the examined eye 10. The light from source 30 is reflected from the mirror 34 is converged to form a real aerial image of the slit lamp light source at 36 between the mirror 34 and the indirect ophthalmoscopy lens 18 used in conjunction with the microscope. The indirect ophthalmoscopy lens acts as a condensing lens to form an image of the light source at approximately secondary focus of the lens 38, such that the light source and its image are conjugate. The indirect ophthalmoscopy lens 18 is thus positioned a distance from the pupil 14 of the examined eye approximately equal to the back focal length of the lens. In this manner, greatest illumination of the fundus 12 can be achieved, to allow a wider field of view of the formed aerial image of the fundus.

Turning to FIG. 3, there is shown a ray tracing depicting spherical aberration of the pupil as it relates to a lens such as the indirect ophthalmoscopy lens 42. This pupil aberration may be thought of as a longitudinal displacement of light rays on the optical axis of the entrance pupil as a function of field angle in the pupil imagery provided by indirect ophthalmoscopy lens 42. Refraction of light rays emanating from entrance pupil 40 by lens 42 do not converge at a point which would coincide with the "pupil" 44 of the slit lamp optics used to view the aerial image of the fundus produced by the indirect ophthalmoscopy lens 42. The eye pupil 40 is thus not correctly imaged to a conjugate point corresponding to the "pupil" of the slit lamp optics at 44, and as such observation using the slit lamp microscope is impaired.

In FIG. 4, the indirect ophthalmoscopy lens of the invention 46 is shown to provide significant correction of pupil aberrations, such that rays emerging from the entrance pupil 40 of a patient's eye will be refracted by lens 46 to a focal area corresponding to the "pupil" 44 of the slit lamp observation optics. In comparison to FIG. 3, the optical characteristics of lens 46 provide for significant correction of pupil aberrations, with light rays originating at the entrance pupil 40 of the eye and incident upon peripheral regions of lens 46 contributing to image formation and observation. The rays proceed to the viewing optical system of the slit lamp microscope in such a way as to be fully utilized and to allow the widest field of view to be obtained while maintaining the substantially aberration-free image of the fundus observed through the slit lamp microscope. This feature of a hand-held indirect ophthalmoscopy lens used in conjunction with the slit lamp, relating to the quality of the imagery of the eye pupil into the slit lamp microscope pupil, has not been recognized in the prior art. If the indirect ophthalmoscopy lens has severe pupil aberrations, the overall image quality will suffer as there will be excessive vignetting of light rays at outer portions of the field of view. The pupil imagery shown in FIG. 4 can be compared with that of FIG. 3, which shows the pupil imagery for a prior art aspherical ophthalmoscopic lens produced by Nikon, having a stated power of 90.1 diopters. The pupil characteristics of this prior art lens, as seen in the ray tracing, demonstrate significant pupil aberration. It should be recognized that light rays passing through the peripheral portion of the prior art Nikon lens, while possibly contributing to image formation do not meet the requirements of good pupil imagery and conjugacy. Rays from the edge of the field of view may completely miss the objective of the slit lamp microscope.

Taking into consideration the effects of pupil aberration, the indirect ophthalmoscopy lens of the invention functions both to correct the primary image quality of the lens, as determined by astigmatism, and also to correct the pupil imagery. Referring back to FIG. 4, the indirect ophthalmoscopy lens 46 of the invention is made of a homogenous transparent material and has a first convex aspheric surface of revolution 60 and a second convex aspherical surface of revolution 62, which together correct both primary image quality as well as pupil aberrations in lens 46. In a single-element double aspheric lens of this type, there are only two design variables of any significant importance which can be adjusted to correct for these aberrations, once the net lens power has been fixed. One of these variables is the lens shape, or "bending" of the lens. The desired net power of the lens, whatever it may be, can be achieved by an infinite variety of lens shapes, which differ in the power attributed to the front surface 60 and the back surface 62 of the lens. Shifting of power from one side of lens to the other provides a continuous variable in design of the lens. The other variable in design consideration is the net amount of aspheric deformation of one or each of the lens surfaces. The lens shape as well as front and back eccentricity values of the novel invention are chosen based on specific design criteria.

With these two design variables, the lens shape, or "bending", and the net amount of aspheric deformation, it is possible to correct for both primary image quality as well a pupil aberrations. In the indirect ophthalmoscopy lens 46 of the invention, the primary image quality of the lens is corrected by the aspheric deformation of surfaces 60 and 62 with the particular correction balanced between the sagittal and tangential astigmatic fields being affected by both the relationships of the power of the front and back surfaces of the lens as well as the distribution of aspheric deformation on the lens surfaces. The design of lens 46 is also corrected for pupil aberrations, resulting in very good pupil imagery with respect to the slit lamp biomicroscope. For a particular net power of the lens, the design of the lens 46 provides optimum field correction as well as correction for pupil aberration, to yield a much improved lens for use with a slit lamp biomicroscope. The surfaces of the lens of the invention are non-symmetrical with respect to one another, which enables correction of both pupil and image aberrations, particularly in larger diameter lenses, which is not achievable in a symmetrical design. The magnitude and shape of each of the surfaces is defined by the polynomial expressed as follows:

$$y = (2rx + (e^2 - 1)x^2)^{\frac{1}{2}} + Ax^F + Bx^G + Cx^H;$$

where r equals the apical radius of curvature of each surface, e equals the apical eccentricity of each surface, and co-efficients A, B, and C equal successive terms in the polynomial, and F, G, and H equal exponents in the successive terms. As an example of the preferred embodiment, for a lens 46 having a focal length of 12.7 mm or net power of 78.71 diopters, and made from a glass having an index of refraction of 1.734, the apical radius of curvature, r, of the front or first surface 60 is 13.18 mm, with an apical eccentricity, e, of 1.053. The back or second surface 62 of this example has an apical radius of curvature of 21.94 mm with an apical eccentricity, e, of 4.864. The thickness of the lens 46 is 9.53 mm. Although the deformation coefficients and exponents have not been specified in this example, these parameters can be used in the lens design in tailoring the sagittal and tangential fields.

In this preferred embodiment, for a lens which is positioned at a distance of 10.40 mm from the eye pupil, and forming an aerial image of the fundus at a position 10.81 mm from the first surface 60 of lens 46, the first to second surface power relationship is established for optimum pupil imagery. In this preferred example, the ratio of the apical radius of curvature of the first surface 60 to the second surface 62 is 1.665, which is reflective of the optimum surface to surface relationship for correcting pupil aberrations when utilizing the aspheric values specified. The lens of this example, being corrected for pupil aberrations, will thus enable light rays incident upon the entire extent of the surface 62 to be converged and contribute to the formation of the aerial image which can then be optimally viewed with a slit lamp biomicroscope. It has been found that When the cone angle in air of the chief rays of each of the bundles of light rays emerging from the eye pupil exceeds approximately 25°, it becomes increasingly important to correct for pupil aberration to enable peripheral regions of the lens to remain useful and to obtain a very wide field of view relative to prior art lenses. The lens of this invention thus enables the full diameter of the lens to remain useful in condensing and image forming functions. With the typical 100 mm focal length of the slit lamp biomicroscope, observation of the fundus aerial image will be adversely affected if pupil aberration is not adequately corrected. In the lens of the invention, the chief rays at the eye pupil are converged by the indirect ophthalmoscopy lens 46 to the "pupil" of the slit lamp optics, corresponding to the working distance of the slit lamp microscope and the focal distance of the objective lens system associated therewith. In this manner, the optimized design of the indirect ophthalmoscopy lens 46 allows the greatest latitude in lens positioning relative to the patient's eye while maintaining good optical quality, and correspondingly, also allows a greater range of adjustment of the slit lamp microscope for examination or treatment of the eye fundus. Thus, the design of the lens for a predetermined net power may vary slightly while still achieving the desired correction of pupil aberrations and imaging characteristics of the lens, as the observer's pupil will allow some slight error in the convergence of light rays at the "pupil" of the slit lamp optics. The correction of both image and pupil aberrations, and the wider field of view obtained with this invention, facilitate a more comprehensive fundus examination and treatment up to 150° in field extent.

Figure 5:
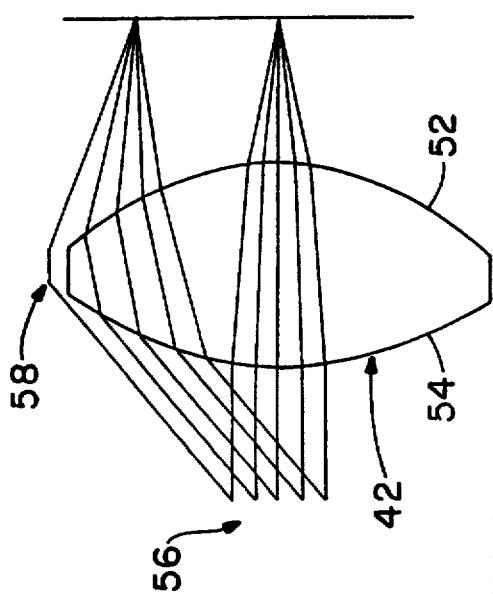
FIG. 5 shows a schematic illustration of tangential ray imaging characteristics in a prior art indirect ophthalmoscopy lens.
Figure 6:
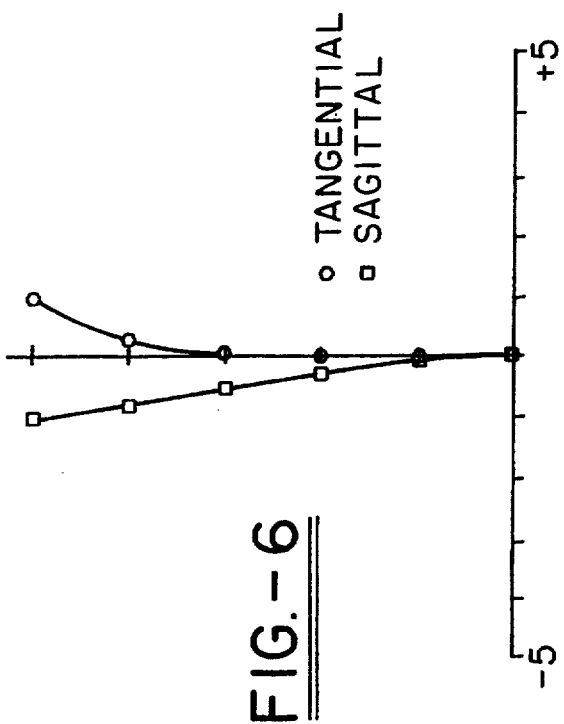
FIG. 6 shows the field curves for the prior art indirect ophthalmoscopy lens shown in FIG. 5.

Turning to FIGS. 5 and 6, the tangential ray imaging characteristics and field curves of the prior an Nikon 90D lens mentioned with respect to FIG. 3 are shown. The lens 42 has a front surface 52, adapted to be positioned toward the observer, having an apical radius of curvature of approximately 9.63 mm and an apical eccentricity of 1.61 as measured with the Form Talysurf Series measuring system produced by Rank Taylor Hobson, Inc. The back surface 54 of lens 42 has an apical radius of curvature of approximately 13.61 mm, and an apical eccentricity of approximately 1.58, while the lens has a center thickness of approximately 11.08 mm and a diameter of approximately 21.95 mm. The index of refraction of the glass used for the lens has been calculated to be 1.621, based on the stated power of 90.1 diopters, thus the glass material is of a typical index of refraction for optical quality glass used for such lenses. For an eye pupil having a diameter of 5 mm as shown at 56, and a pupil to lens distance of 7.5 mm, it is noted that the physical characteristics of the lens 42 result in vignetting of light rays 58 contributing to the peripheral field of view. This prior art lens will form an aerial image at a position 7.64 mm from anterior surface 52, with some reduction of those bundles contributing to the peripheral portion of the aerial image. The field curves for the prior art Nikon 90D lens indicate that the tangential field is well corrected, while the sagittal astigmatic field curve is slightly less well corrected. Although the field curves of the Nikon 90D lens do show that the lens is relatively well corrected for overall image quality, the lens has not been corrected for pupil aberrations as indicated in FIG. 3. The field of view and the resolution of the image observed through a slit lamp microscope will therefore be adversely affected, to result in less than optimum performance in use with a slit lamp microscope.

The pupil imagery of another prior art lens is shown in FIG. 7, which relates to a 90D lens produced by Volk Optical, Inc. The lens 70 includes two symmetrical aspheric surfaces 72 and 74, each having an apical radius of curvature of a 11.622 mm and an apical eccentricity of 1.543. The center thickness of the lens 70 is 8.763 mm, and the lens has a diameter of 21.55 mm and is constructed of a glass having an index of refraction of 1.523. The imaging characteristics of the prior art Volk 90D lens indicate that again the image aberrations have been relatively well corrected and although this lens shows better pupil characteristics than the Nikon 90D lens (as seen in FIG. 3), significant pupil aberration remains, relating particularly to those chief rays proceeding from the peripheral portions of the aerial image. Again, although the primary image quality has been corrected to a significant degree, pupil aberrations have not been fully corrected, resulting in less than optimum performance for use with a slit lamp biomicroscope.

Figure 9:
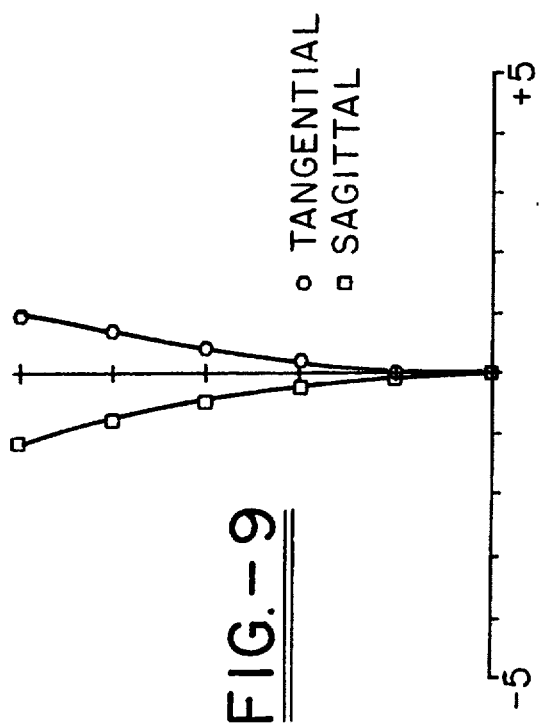
FIG. 9 shows the field curves for the indirect ophthalmoscopy lens as shown in FIG. 8.

Turning to FIGS. 8 and 9, the imaging characteristics of the indirect ophthalmoscopy lens 46 referred to in FIG. 4, in accordance with the preferred example given above, are shown. For an eye pupil of 5 mm, and with the lens positioned 10.40 mm from the eye pupil, the imaging characteristics of lens 46 are optimized, with pupil aberrations at the "pupil" 44 of the slit lamp microscope optics being substantially eliminated (shown in FIG. 4). In the figures, the propagation of light rays within the optical systems of this invention have been ray traced using accepted mathematical models of the human eye. Although shown as proceeding as parallel bundles from an entrance pupil location in air, the ray tracings correspond to light rays which originate at the retina and proceed through the vitreous humour, crystalline lens, aqueous humour and cornea of the eye to the various lens elements of the invention embodiments. The use of said parallel bundles in air is a simplified representation of the more complex optical system involving the examined human eye, but in fact realizes an identical optical system model as that of an average human emmetropic eye, and is shown represented in all optical system layouts herein. It should be recognized that refractive errors of the eye may require adjustment of the indirect ophthalmoscopy lens system and/or observing microscope, but the imaging characteristics of the lens system remain consistent. As seen in FIG. 9, the astigmatic field curves of the lens 46 indicate that the lens is well corrected for primary image quality, with the sagittal field being made as flat as possible while still correcting for pupil aberrations in the lens. Thus, the lens has been optimized in terms of both primary image quality as well as pupil imagery. With the design variables of surface power and aspheric surface deformation, both aberrations affecting primary image quality and pupil aberrations are corrected in a unique set of parameters for a lens of a given power. The characteristics of the lens may change if the index of refraction of the lens glass or plastic is modified, the center thickness is independently changed, or if the net lens power is changed. When it is desired to obtain a fundus image of greater or lesser magnification in order to facilitate a more comprehensive fundus diagnosis, the system focal length or dioptric power must be appropriately changed. To obtain a fundus image of greater magnitude and actual size, a lens of lower power may be utilized, and conversely to obtain a very wide field fundus image a lens of higher power may be used. With maximum potential field of view kept at a constant for lens powers ranging from 50 to 150 diopters, it has been found that the surface to surface radii relationship and surface to surface eccentricity relationship remains essentially constant in the optimization of the lens design. Whether a higher or lower power lens is considered within the 100 diopter range mentioned, other than a change in diameter, center thickness, and surface vertex radii, the front to back radii ratio will remain essentially identical to the already proposed model, as will the front-to-back eccentricity ratio and actual eccentricity values. Slight modifications in eccentricity may be desired to compensate for the fact that the distance from the image to the slit lamp pupil remains constant while the distance from the lens to the formed aerial image changes as front focal length is changed.

Figure 11:
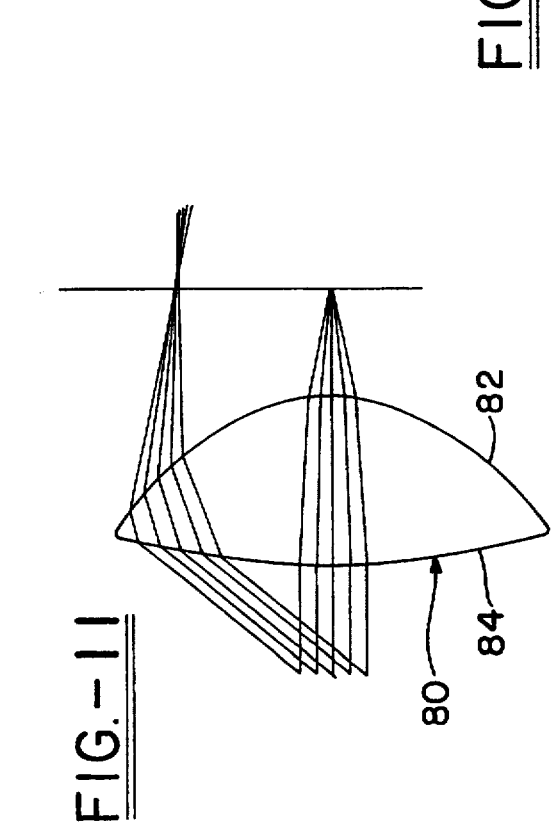
FIG. 11 shows a schematic representation of tangential ray imaging characteristics for the indirect ophthalmoscopy lens as shown in FIG. 10.
Figure 12:
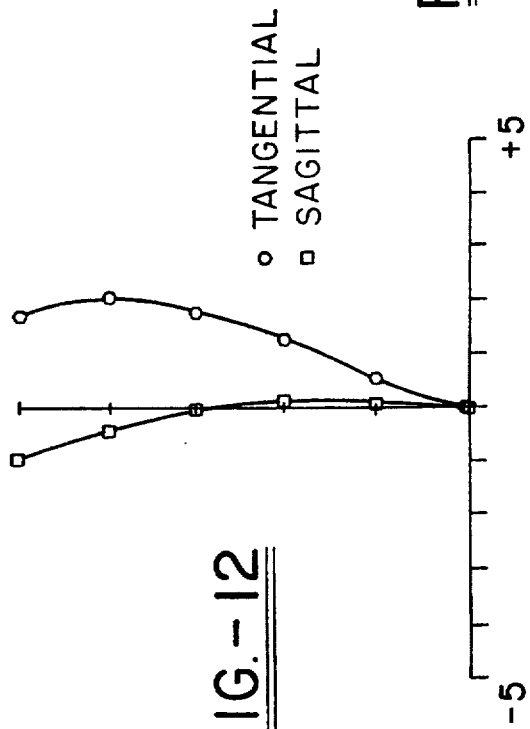
FIG. 12 shows the field curves for an indirect ophthalmoscopy lens as shown in FIG. 10.

Turning now to FIGS. 10–12, another example of the indirect ophthalmoscopy lens in accordance with the invention is shown. In this example, the lens has a net power of approximately 110 diopters, with a 9.1 mm focal length and is designed to provide a field of view even greater than the previously described lens of FIGS. 4, 8 and 9. At this net power, the lens design also provides excellent pupil imagery as seen in FIG. 10. The lens 80 is made of an optical material having an index of refraction of 1.734, and has a thickness of 10.50 mm and diameter of 24.0 mm. The lens 80 has a first surface 82, having an apical radius of curvature, r, of 8.365 mm, and an apical eccentricity, e, of 1.0753. The second surface 84 has an apical radius of curvature 15.480 mm and an apical eccentricity of 5.547. For a 5 mm eye pupil, and a distance from the eye pupil to the lens of 5.91 mm, the imaging characteristics are shown to be relatively well corrected. Also, as shown in FIG. 12, the field curves for the lens of this example indicate that the lens is relatively well corrected for field aberrations, particularly with respect to the sagittal field.

Figure 13:
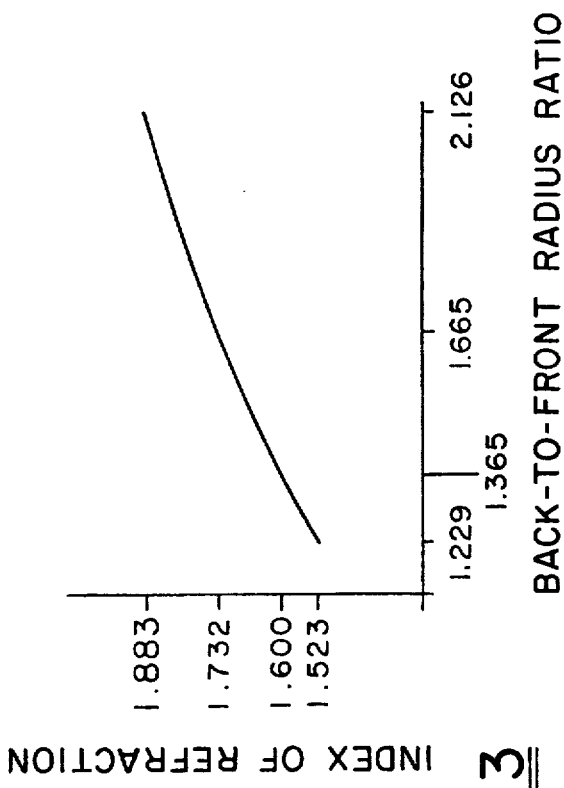
FIG. 13 shows a plot of the index of refraction of an indirect ophthalmoscopy lens of the invention versus the back to front radius ratio of the lens surfaces.
Figure 14:
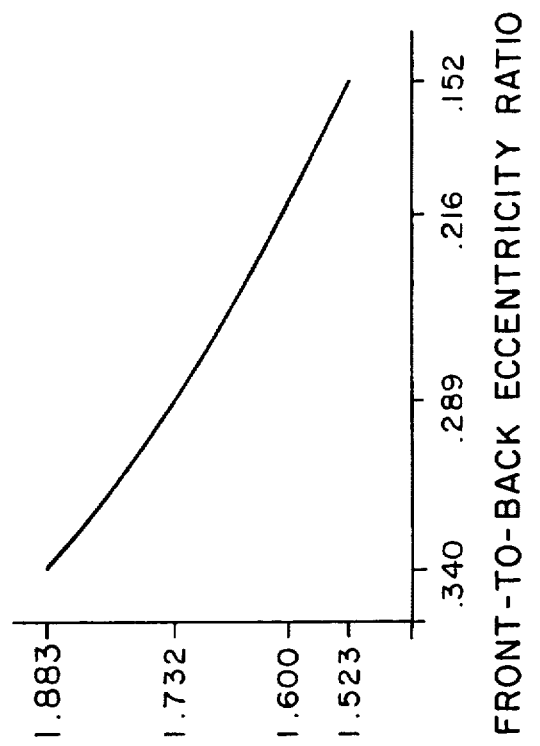
FIG. 14 shows a plot of the index of refraction of an indirect ophthalmoscopy lens in accordance with the invention versus the front to back eccentricity ratio of the surfaces.

Turning now to FIGS. 13 and 14, there are shown plots of the relationship of the index of refraction of the material from which the indirect ophthalmoscopy lens is made, relative to the back to front surface vertex radius ratios and the front-to-back surface apical eccentricity ratios for the lens design of the invention. In FIG. 13, there is seen a front-to-back surface power increase as index of refraction increases. Similarly, as seen in FIG. 14, the front-to-back eccentricity ratio decreases with increasing index of refraction, indicating a progressive increase in the back surface eccentricity as the index of refraction increases. Various lens values have been calculated for representative cases of four different values of index of refraction. These values are based on lenses designed in accordance with the invention, all four designs having the same focal length, 12.68 mm, and with each lens corrected in an identical manner. The lens values include surface vertex radii, thickness, and front and back apical eccentricity. The lens diameter is 27 mm in each case, and the lens thicknesses were chosen to give approximately the same edge thickness at the outer rim of the lens. The lens designs are shown in Table I below:

TABLE I

| | INDEX OF REFRACTION | | | |
|---|---|---|---|---|
| | n = 1.523 | n = 1.600 | n = 1.734 | n = 1.883 |
| Front Radius | 9.48 mm | 10.99 mm | 13.18 mm | 15.10 mm |
| Back Radius | 11.65 mm | 15.00 mm | 21.94 mm | 32.11 mm |
| Thickness | 13.00 mm | 11.50 mm | 9.53 mm | 8.25 mm |
| Front Eccentricity | 1.033 | 1.039 | 1.053 | 1.074 |
| Back Eccentricity | 3.039 | 3.590 | 4.864 | 7.087 |
| Ratio of Radii | 1.229 | 1.365 | 1.665 | 2.126 |

From the results as indicated in Table I, the front surface of the lens is seen to have an optimum eccentricity in the range from 1.0–1.1, which is almost independent of refractive index. The aerial image quality as well as the pupil imagery is identical in all four examples.

Based upon the foregoing, the relationships between the apical radii of curvature of the surfaces and the apical eccentricities provide the basis for optimal correction of both primary image quality and pupil aberrations. It has been found that if the at least one lens element is made from a material having an index of refraction in the range from 1.45 to 1.95, the ratio of the apical radius of curvature of the first and second surfaces may be in the range of 0.9 to 2.6, and the ratio of the apical eccentricity of the first and second surfaces may be in the range of 0.075 to 0.55, for lenses having a net power in the range of 50 to 150 diopters. Best correction of these aberrations is achieved by a ratio of the apical radius of curvature in the range from 1.2 to 2.3, and a ratio of the apical eccentricity in the range from 0.1 to 0.4. For a material having an index of refraction of approximately 1.523, the ratio of the apical radius of curvature of the first and second surfaces may be in the range of 0.9 to 1.8, and the ratio of the apical eccentricity of the first and second surfaces may be in the range of 0.15 to 0.55 for lenses having a net power of 50 to 150 diopters. Best correction of the field and pupil aberrations is achieved by a ratio of the apical radius of curvature in the range of 1.2 to 1.5, and a ratio of apical eccentricity in the range of 0.3 to 0.4. For a material having an index of refraction of approximately 1.60, the ratio of the apical radius of curvatures may be in the range of 1.0 to 1.9, and the ratio of the apical eccentricities may be in the range of 0.145 to 0.435 for lenses having a net power of 50 to 150 diopters. Best correction of these aberrations is achieved by a ratio of the apical radii of curvature in the range of 1.3 to 1.6, and a ratio of apical eccentricities in the range of 0.25 to 0.35. For a material having an index of refraction of approximately 1.734, the ratio of the apical radius of curvatures may be in the range of 1.3 to 2.2, and the ratio of the apical eccentricities may be in the range of 0.1 to 0.325 for lenses having a net power of 50 to 150 diopters. Best correction of these aberrations is achieved by a ratio of the apical radii of curvature in the range of 1.6 to 1.9, and a ratio of apical eccentricities in the range of 0.15 to 0.25. For a material having an index of refraction of approximately 1.883, the ratio of the apical radius of curvatures may be in the range of 1.8 to 2.6, and the ratio of the apical eccentricities may be in the range of 0.075 to 0.25 for lenses having a net power of 50 to 150 diopters. Best correction of these aberrations is achieved by a ratio of the apical radii of curvature in the range of 2.0 to 2.3, and a ratio of apical eccentricities in the range of 0.1 to 0.2.

Another embodiment of the indirect ophthalmoscopy lens of the invention is shown in FIGS. 15a–e, showing a compound lens design using at least two lens elements. It has been found that a compound lens comprising two positive spherical surfaced lenses nearly in contact with one another can provide substantial correction of aerial image quality or the pupil image quality of the lens, but both aerial image quality and pupil image quality cannot be optimized simultaneously with such a design. The indirect ophthalmoscopy lens of the invention therefore utilizes at least one aspherical surface in association with one of the lenses of the compound lens to allow further degrees of freedom to simultaneously correct for both primary image quality as well as pupil imagery. In FIGS. 15a–e, examples of compound lens designs which allow correction of both primary image quality and pupil imagery are shown. As seen from the examples in FIGS. 15a–e, a first lens element 80 is positioned adjacent to the patient's eye to be examined. The lens 80 has a posterior surface 82 and an anterior surface 84. A second lens 86 is positioned in relatively close proximity to lens 80, and also includes posterior surface 88 and anterior surface 90 associated therewith. In general, the preferred embodiment will provide the lens 80 having its anterior surface 84 as being more highly curved than the posterior surface 82. Indeed, posterior surface 82 may comprise a plano surface as shown in FIG. 15a, or alternatively a convex aspherical surface as shown in FIG. 15d or a concave surface as shown in FIG. 15e. In the preferred embodiment, the anterior surface 84 of lens element 80 is designed as a convex surface which is more highly curved than the opposed posterior surface 88 of lens element 86. As such, it contributes to the correction of both primary image quality and pupil imagery of the compound lens accordingly. Thus, as is seen in the examples of FIGS. 15a–e, the posterior surface 88 of lens element 86 may be plano or convex, and if convex, will have a flatter curve than convex anterior surface 84 of lens element 80. This particular configuration helps to minimize reflections while still providing desired corrective qualities in the lens. As is also seen in the examples of FIGS. 15a–e, the anterior surface 90 of lens element 86 may be convex or plano, being the surface of the indirect ophthalmoscopy lens which faces the observer. As seen in the FIGS. 15a–e and the light ray pathways schematically represented, lens element 80 may be of smaller diameter than lens element 86 while still performing its optical function in capturing and refracting light rays emerging from the eye. Lens element 80 may also be of higher power to facilitate obtaining an extremely wide field of view as desired.

In the examples of FIGS. 15a–e, particular typical designs which have been found to correct for both primary image quality as well pupil imagery are shown in Table II below:

TABLE II

|  | FIG. 15a | FIG. 15b | FIG. 15c | FIG. 15d | FIG. 15e |
|---|---|---|---|---|---|
| Distance from Eye Pupil to Surface 82 | 9.70 mm | 9.46 mm | 9.95 mm | 9.90 mm | 9.61 mm |
| Radius of Surface 82 | Plano | Plano | Plano | 100.00 mm | −50.00 mm |
| Thickness of Lens 80 | 7.00 mm | 8.00 mm | 8.00 mm | 8.50 mm | 6.50 mm |
| Radius of Surface 84 | 12.78 mm | 12.65 mm | 12.32 mm | 12.45 mm | 11.92 mm |
| Eccentricity of Surface 84 | 1.2048 | 1.0070 | .9660 | 1.1699 | .8101 |
| Air Gap Between Lenses 80 & 86 | .50 mm | .50 mm | .50 mm | .50 mm | .50 mm |
| Radius of Surface 88 | Plano | 61.30 mm | 36.88 mm | 83.42 mm | 47.50 mm |
| Thickness of Lens 86 | 5.00 mm | 5.00 mm | 4.50 mm | 4.50 mm | 5.50 mm |
| Radius of Surface 90 | 27.54 mm | 61.30 mm | Plano | 83.42 mm | 47.50 mm |
| Distance to Aerial Image | 10.21 mm | 9.76 mm | 9.71 mm | 9.43 mm | 10.40 mm |

In the typical examples of compound indirect ophthalmoscopy lenses in accordance with the invention as shown in FIGS. 15a–e, making at least one of the convex surfaces provided on one of the lenses aspherical allows correction of both primary image quality as well as pupil imagery in the lenses. In these examples, both lens elements are made of a high-index of refraction glass ($N_d = 1.734$), but it is contemplated within the invention that either one or both lens elements be made of either ophthalmic glass or plastic of any available index of refraction. In the typical design examples shown in FIGS. 15a–e, the convex anterior surface 84 of lens 80 is shown as the aspheric surface, which in these examples is a pure conic aspheric surface. In the compound lens design, it has been found that it makes little difference which of the four available surfaces of the lenses the aspheric surface of revolution is provided on, and it is also contemplated that more than one aspheric surface may be provided to obtain similar performance characteristics. Similarly, all of the compound lens designs as shown in FIG. 15 have a similar focal length, being approximately 12.7 mm, but it is understood that the focal length of the lens may be adjusted if desired by varying the parameters of one or more of the lenses accordingly. In the preferred embodiment, surface 84 of lens 80 will be provided as an aspheric surface, with surface 82 being of either convex or concave design. Surfaces 88 and 90 of anterior lens 86 may be plano or convex as shown, with the particular surfaces chosen to be compatible with the aspheric surface provided on surface 84 as an example.

Figure 16:
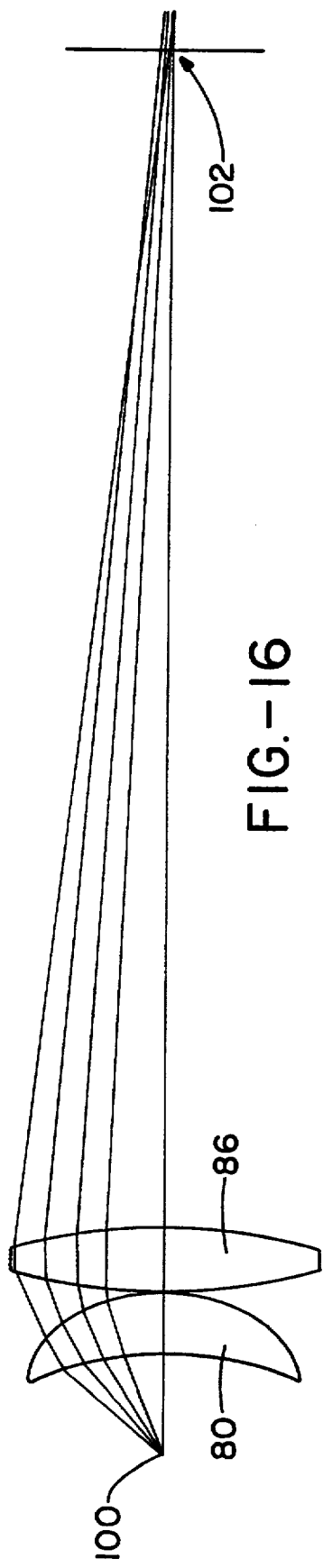
FIG. 16 shows the pupil imagery of an indirect ophthalmoscopy lens of the invention incorporating the compound lens design.
Figure 18:
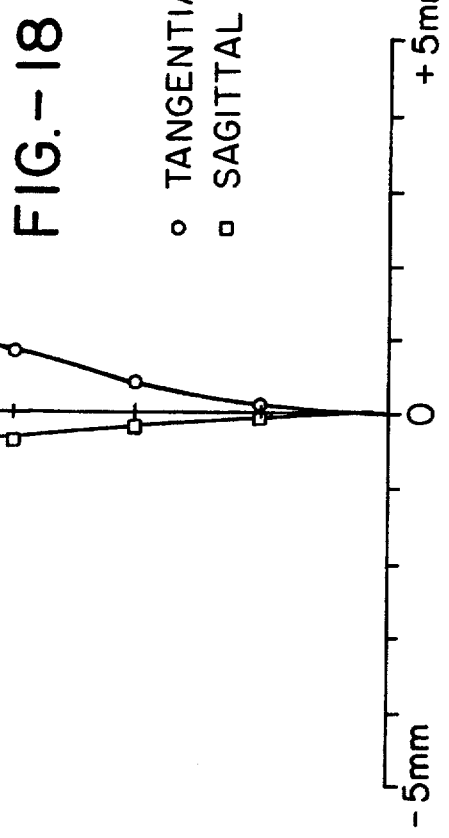
FIG. 18 shows the field curves for an indirect ophthalmoscopy lens in accordance with the invention as shown in FIG. 17.
Figure 17:
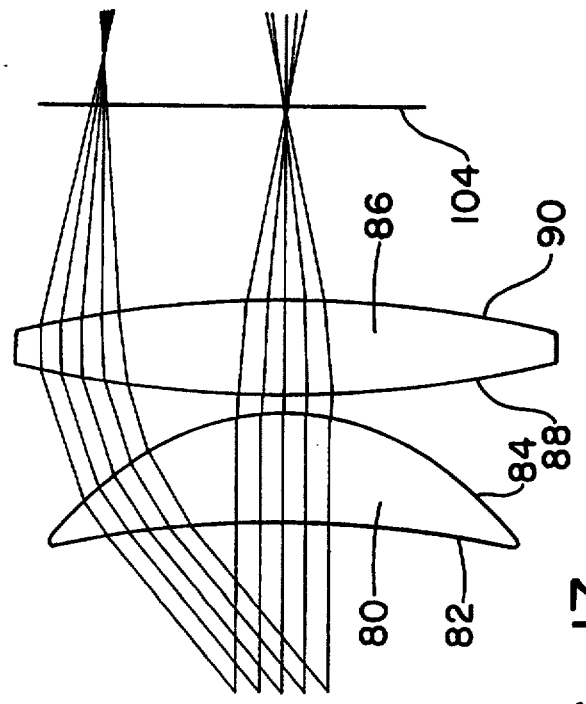
FIG. 17 shows a schematic representation of tangential ray imaging characteristics for an indirect ophthalmoscopy lens in accordance with the invention as shown in FIG. 16.

In the compound indirect ophthalmoscopy lens design, FIG. 16 shows the pupil imagery characteristics of each of the typical examples shown in FIGS. 15a–e. The compound lens design is shown to provide significant correction of pupil aberrations, such that rays emerging from the pupil 100 of a patient's eye will be refracted by lens 80 toward lens 86, which further refracts light rays to a focal area corresponding to the "pupil" 102 of the slit lamp observation optics. The imaging characteristics of the typical compound indirect ophthalmoscopy lens in accordance with the invention are shown in FIGS. 17 and 18, wherein for an eye pupil of 5 mm diameter, and with the posterior lens element 80 positioned approximately 10 mm from the eye pupil, light rays emerging from the fundus of the eye will be refracted by the compound lens to form an aerial image at an image plane 104 approximately 10.5 mm from surface 90 of lens element 86. The example of the compound lens as shown in FIG. 17 utilizes glass lenses 80 and 86 having an index of refraction of n = 1.734, with surface 82 being concave and having a radius of curvature of 33.9 mm. Surface 84 is an aspheric surface of revolution, having a radius of curvature of 11.5 mm and an eccentricity of 0.8916. The lens element 80 is approximately 6.0 mm thick, and there is an air gap between lenses 80 and 86 of approximately 0.5 mm. The lens element 86 includes spherical surfaces 88 and 90 having a radii of curvature of 43.2 mm and a thickness of 6.0 mm. The compound lens of this design will have a 12.7 mm system focal length, and again may be modified to include additional aspheric surfaces if desired. Additionally, the characteristics of each of the lenses 80 and 86 may change if the index of refraction of the lens glass or plastic is modified, the center thickness is independently changed or if the net lens power is changed. Similarly, the system focal length or dioptric power of the lens system may be changed to obtain greater or lesser magnification as desired. As seen in FIG. 18, the astigmatic field curves of the compound lens indicate that the lens is well corrected for primary image quality, while the correction of pupil aberrations is achieved as indicated by the pupil imaging characteristics shown in FIG. 16. It is again reiterated that although surface 84 of lens element 80 has again been shown as an aspheric surface, allowing the degrees of freedom to correct for both primary image quality and pupil imagery in the lens, it is contemplated that additional lens surfaces may be aspheric surfaces which combine to yield the desired correction and performance characteristics similar to the examples shown. For reasons relating to simplicity in manufacturing, the preferred embodiments shown utilize a single convex aspheric surface, having an apical radius of curvature in the range between 10 and 15 mm, with an apical eccentricity in the range from 0.5 to 1.5. The radii of the surfaces of the anterior lens element 86 determine the aspheric curve needed to obtain both good primary image quality as well as correction of pupil aberration.

Turning now to FIG. 19, an ophthalmoscopic contact lens device is shown incorporating the optical qualities aforementioned in accordance with the invention. In this embodiment, a contact lens 110 includes a posterior surface 112, which in the preferred embodiment will have an aspheric curve corresponding to that of the average cornea of a human eye. The contact lens 110 further includes an anterior surface 114, which is a convex surface of spherical or aspherical design. As shown in FIG. 19, anterior to contact lens 110 may be one or more lens elements, which as shown may comprise a compound lens of two or more elements similar to that described with reference to the embodiments of FIG. 15. In such an embodiment, lens 80 may be produced of a plastic material to simplify the manufacturing process. As an anterior lens 86 will effectively protect internal lens 80 within the housing supporting the three or more lens elements, lens 80 will not be exposed to scratching or other damage that may occur, thus permitting the use of softer materials such as ophthalmic plastic. Alternatively, a single anterior lens element as shown in FIGS. 8 and 11 may be similarly combined with a contact element, providing an ophthalmoscopic contact lens device incorporating optical qualities in accordance with the invention. The contact lens 110 may be provided with positive dioptric power to enable imaging of an extremely wide field of view of the fundus of the examined eye.

It is also a feature of the present invention to provide an indirect ophthalmoscopy lens system which can be adapted for various diagnostic or treatment uses in a simple and effective manner. Particularly, given an indirect ophthalmoscopy lens having a nominal power to achieve predetermined magnification and imaging characteristics, it is desirable to enable adaptation of such a lens to a system providing altered magnification and field characteristics for various imaging requirements. The invention therefore provides a series of positive and negative power adapter lenses and lens systems to serve as attachments to an indirect ophthalmoscopy lens. In one aspect of this embodiment, it is desired to change the net power of the indirect ophthalmoscopy lens system while simultaneously retaining both good retinal as well as good pupil imagery. The adapter lens system may also be used to modify the performance of an indirect ophthalmoscopy lens so as to optimize the pupil imagery of the lens system.

Figure 20:
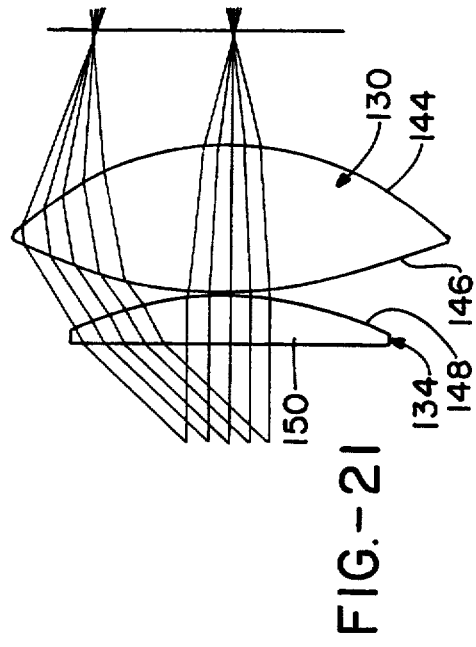
FIG. 20 shows an alternate embodiment of the invention wherein an indirect ophthalmoscopy lens is selectively combined with an adapter lens system to vary the nominal power and/or imaging characteristics of the indirect ophthalmoscopy lens.

As seen in FIG. 20, an indirect ophthalmoscopy lens 130 may be a lens having characteristics as described herein, or may be any other conventional hand-held indirect ophthalmoscopy lens system used for imaging the fundus of the eye. The hand-held indirect ophthalmoscopy lens 130 is positioned within a conventional retainer housing 132, and is thus designed to have a predetermined nominal power. The adapter lens system of the invention comprises one or more additional lenses 134 mounted in an adapter housing 136. The housing 136 may be selectively attached to the housing 132 of the indirect ophthalmoscopy lens 130 for use in conjunction therewith. For attachment to the indirect ophthalmoscopy lens housing 132, the adapter lens housing 136 may include an engagable flexible section 138 having an outer diameter slightly larger than the inner diameter of housing 132, for engagement therewith. For example, a compressible and resilient o-ring 140 may be used to frictionally engage the inner surface of housing 132, thus sealing the interior space between adapter lens 134 and the indirect ophthalmoscopy lens 130. In the preferred embodiment, the formed air and water-tight seal serves to protect the lens surfaces from water or contamination as well as simplify cleaning after use. The o-ring 140 may be integrally formed in the adapter housing section 138, or may be provided as a separate member set in a groove machined around the circumference of area 138. As an alternative to an o-ring member 140, other engagement means such as resilient engaging fingers or other suitable structure such as engaging thread systems may be used in association with adapter lens housing 136 or housing 132 as desired. Also in the preferred embodiment, the adapter lens housing 136 also includes an outer diameter section which is slightly larger than that of the indirect ophthalmoscopy lens housing 132 to provide a "catch" 142 allowing the adapter to be easily and selectively removed. Such a catch 142 may be provided at another location on the housing 136 if desired.

Figure 21:
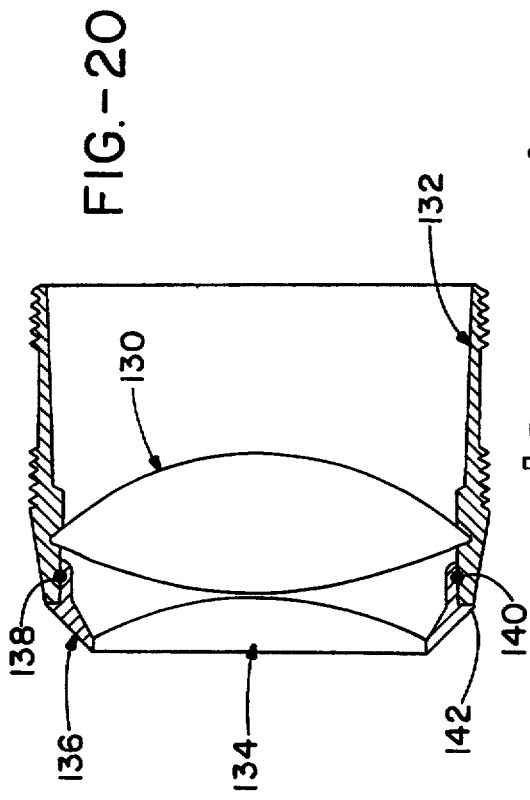
FIG. 21 shows a schematic representation of the tangential ray imaging characteristics for an indirect ophthalmoscopy lens and adapter lens system in accordance with the invention.
Figure 22:
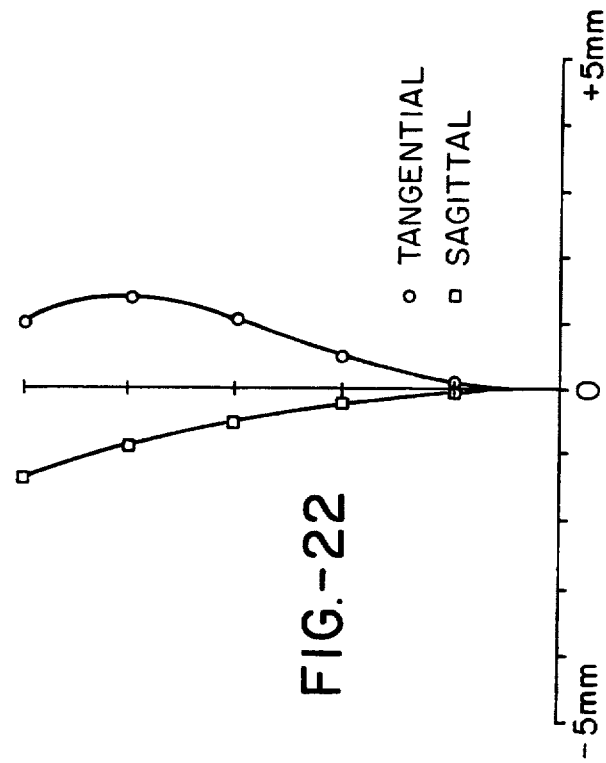
FIG. 22 shows the field curves for an indirect ophthalmoscopy lens in conjunction with the adapter lens system as shown in FIG. 21.
Figure 23:
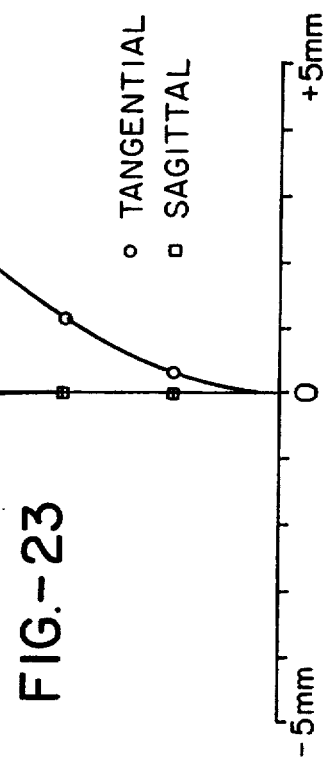
FIG. 23 shows the field curves for an alternate design of the adapter lens shown in FIG. 21.
Figure 24:
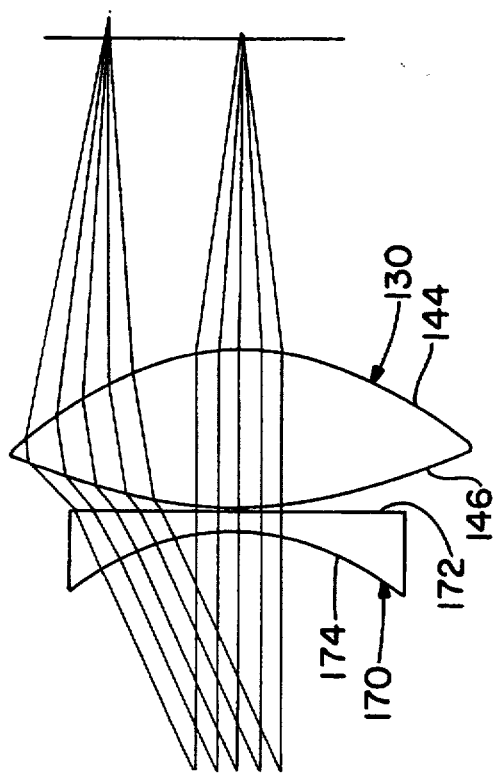
FIG. 24 shows an alternate embodiment of the adapter lens system for use with an indirect ophthalmoscopy lens and the tangential ray imaging characteristics thereof.
Figure 25:
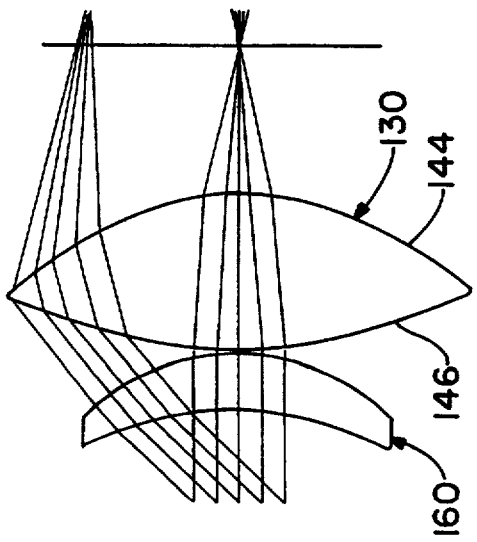
FIG. 25 shows the field curves for the adapter lens system as shown in FIG. 24.

Turning to FIG. 21, there is shown the retinal imagery characteristics of an indirect ophthalmoscopy and lens adapter system such as that shown in FIG. 20. In this example, the indirect ophthalmoscopy lens 130 is formed from any suitable optical material. In a particular example, the material of lens 130 may have an index of refraction of 1.734, with the lens having a diameter of approximately 27.10 mm, and a center thickness of approximately 9.41 mm. The lens 130 may be bi-convex, with a first surface 144 designed as an aspheric surface of revolution having an apical radius of curvature of 14.39 mm and an eccentricity of 1.275. The other surface 146 of lens 130 may also be an aspheric surface of revolution having an apical radius of 18.82 mm and an eccentricity of 2.62. The adapter lens 134 is shown schematically positioned relative to lens 130 by means of the adapter lens housing 136 as previously described. The lens 134 may be formed of optical grade plastic, such as poly methyl methacrylate (PMMA), or can be made of glass or other suitable material as desired. A space between lenses 130 and 134 of 0.25 mm may be maintained upon insertion of the adapter lens housing 136 into the housing 132 of indirect ophthalmoscopy lens 130. In this embodiment, a single adapter lens 134 is utilized, being a plano-convex glass lens designed to add positive refractive power to the system in use with the indirect ophthalmoscopy lens 130. Alternatively, the plano side of the lens may be concave or convex if desired. The lens 134 has a first convex surface 148 which may be spherical or aspherical, facing indirect ophthalmoscopy lens 130. In the embodiment shown in FIG. 21, the surface 148 is spherical, having a radius of 24.55 mm, with a diameter of 20.5 mm, and a center thickness of 3.129 mm. The retinal imaging characteristics for the indirect ophthalmoscopy lens 130 used in association with the adapter lens 134 are shown in FIG. 21, indicating excellent imaging characteristics. The field curves for the system of FIG. 21 are given in FIG. 22, wherein it is noted that a relatively flat sagittal field is obtained with good imaging in the tangential field. It may be desirable to further flatten the sagittal field in the lens system, in order to avoid a convexed or pincushion appearance of the aerial fundus image and thus the convex surface 148 of the adapter lens 134 may be formed as an aspheric surface to obtain further correction of this type. In this particular embodiment, to flatten the sagittal field requires a relatively strong aspheric surface, with an example being a conicoid aspheric surface having an eccentricity of 3.5. The imaging characteristics of such an adapter lens in use with the indirect ophthalmoscopy lens 130 are shown in FIG. 23, wherein it is noted that the sagittal field has been substantially flattened. As another example, FIG. 24 shows a meniscus adapter lens 160 using spherical surfaces. This adapter lens also provides good imaging characteristics in use with lens 130 as shown by the field curves of FIG. 25.

In the embodiments of the adapter lens as described above, each of the adapter lenses 134 and 160 have a nominal power of approximately 20 diopters so as to add power to the lens system when used in association with the indirect ophthalmoscopy lens 130. When the adapter lenses 134 or 160 are used with an indirect ophthalmoscopy lens 130 as described, the substantial thickness of the indirect ophthalmoscopy lens system thus created results in a net power which is less than the combined nominal powers of adapter lens 134 or 160 and indirect ophthalmoscopy lens 130. Particularly, in this example the lens 130 has a power of 79.2 diopters, and the addition of the adapter lenses 134 and 160, having a nominal power of 20 diopters, result in a net system power of 93.3 diopters, or an increase of approximately 14 diopters to the net system power. The net power is thus selected for a particular diagnostic or treatment application, with the adapter lenses utilized to expand the function of the indirect ophthalmoscopy lens 130.

Figure 26:
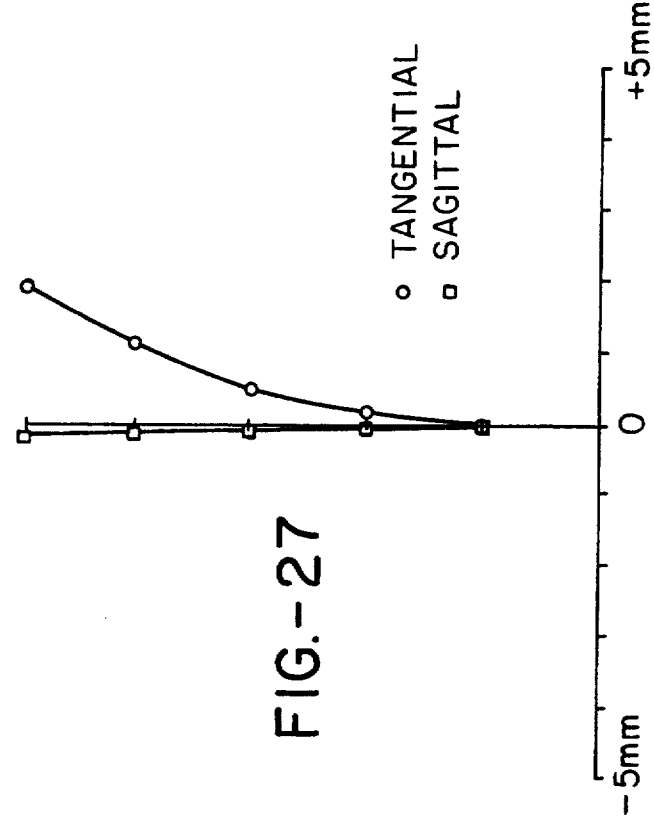
FIG. 26 shows an alternate embodiment of an adapter lens system for use in association with an indirect ophthalmoscopy lens, including the tangential ray imaging characteristics thereof.
Figure 27:
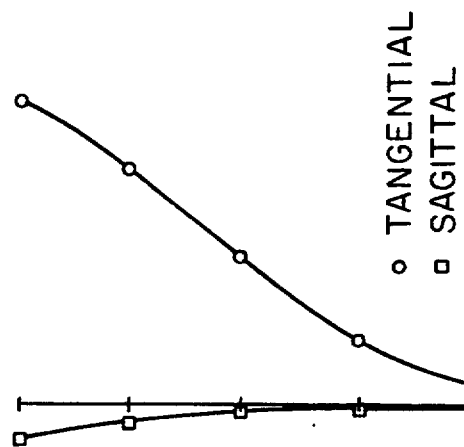
FIG. 27 shows the field curves for the adapter lens system as shown in FIG. 26.

Turning to FIG. 26, a minus power adapter lens 170 having a plano side 172 and a concave side 174 is selectively positioned relative to indirect ophthalmoscopy lens 130 to reduce the power of the system. As an example, the adapter lens 170 may be a lens having a nominal power of −37 diopters and a center thickness of approximately 1 mm. Using a negative power lens provides an opportunity to partially or fully correct for the chromatic aberration of the indirect ophthalmoscopy lens system by using a highly dispersive optical material, such as a flint glass. Other glass or plastic materials may be used as well, as depicted in the following example using BK7 glass. The concave surface 174 may have a diameter of approximately 20 mm, a radius of curvature of 13.27 mm, and an eccentricity of 1.1. The use of an aspherical concave surface provides proper correction for retinal and pupil imagery in combination with the indirect ophthalmoscopy lens 130. In use with lens 130, the adapter lens provides a net power of the system of approximately 55.2 diopters or approximately 24 diopters less than the power of lens 130. The field curves of the system including lens 170 are shown in FIG. 27, indicating good performance of the type previously described. Alternatively, opposite surface 172 may be aspherized and made to progressively increase in curvature similarly correcting image aberrations while the posterior concave surface 174 is produced as a sphere.

Figure 28:
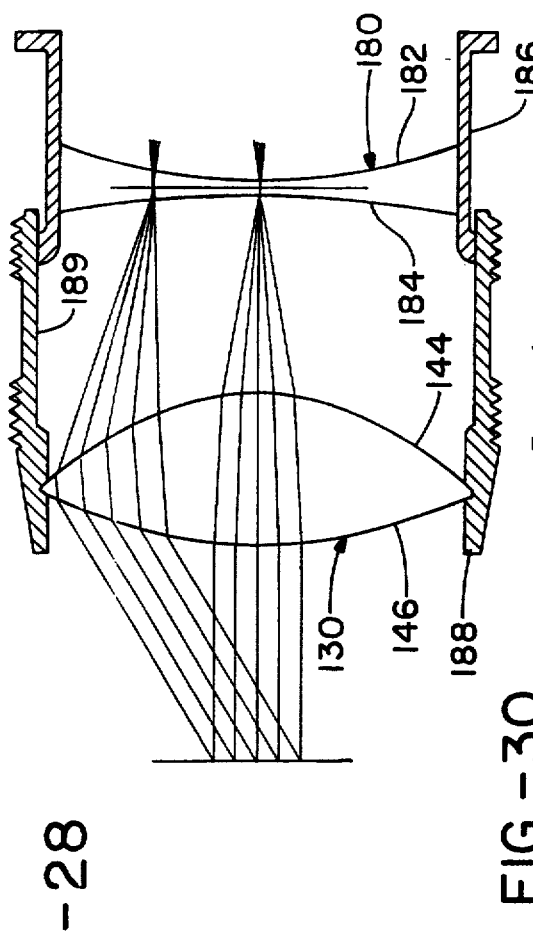
FIG. 28 shows an alternate embodiment of an adapter lens system for use in conjunction with an indirect ophthalmoscopy lens, including the tangential ray imaging characteristics thereof.
Figure 29:
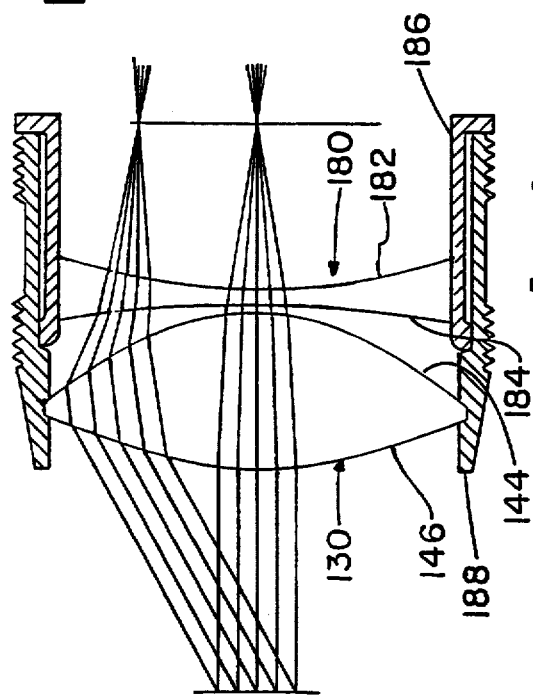
FIG. 29 shows the field curves for the adapter lens system as shown in FIG. 28.

In an alternate preferred embodiment using a minus powered lens of slightly increased diameter, the adapter lens itself is positioned on the anterior side of the indirect ophthalmoscopy lens. This relative lens positioning likewise provides for correction of the field characteristics of the combination lens system, using simple planar and/or spherical surfaces, while maintaining the optimum pupil characteristics required for use with the slit lamp biomicroscope. As in previous embodiments, the adapter lens system provides selective attachment of the adapter lens system to an indirect ophthalmoscopy lens system by means of lens housings which are selectively attached to one another. Referring the FIG. 28, a minus power adapter lens 180 with a concave surface 182 and concave surface 184 is supported in an adapter lens housing 186, which is selectively attached to the housing 188 of an indirect ophthalmoscopy lens system. Adapter lens 180 is selectively positioned adjacent to the more highly curved surface 144 of the indirect ophthalmoscopy lens 130 such that the power of the combination lens system is reduced relative to that of the indirect ophthalmoscopy lens 130 when used alone. In this embodiment, lens 180 and its associated housing 186 are manually adjustable and selectively positioned relative to indirect ophthalmoscopy lens 130 and lens housing 188 along the axis of lens 130. This adjustable positioning of lens 180 provides adjustment of the distance between lenses 130 and 180 to change the total system power. In an example of the embodiment of FIG. 28, adapter lens 180 has a nominal power of −21 diopters, a center thickness of approximately 1 mm, and a diameter of 26.4 mm. The concave surface 184 may be produced with a radius of 74 mm and concave surface 182 produced with a radius of 40 mm. In FIG. 28, lens 180 is shown positioned with surface 184 separated from surface 144 of lens 130 by approximately 0.5 mm, resulting in a net system power of approximately 65 diopters, being approximately 14 diopters less than the power of lens 130. Field curves of the system including lens 180 are shown in FIG. 29, again indicating good performance of the type previously described.

Figure 30:
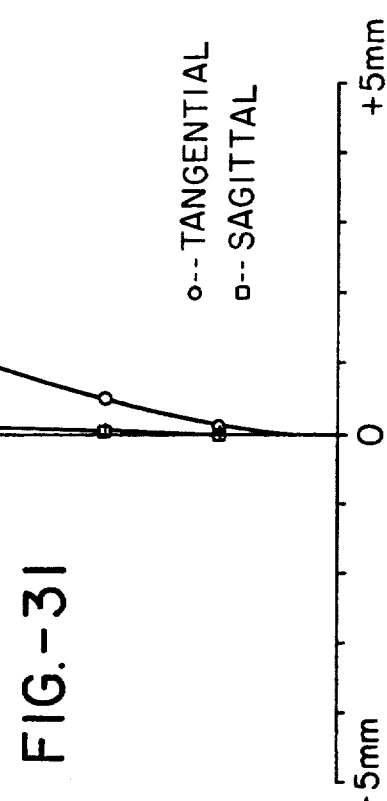
FIG. 30 shows the adapter lens of FIG. 28 with the lens repositioned in the optical system.
Figure 31:
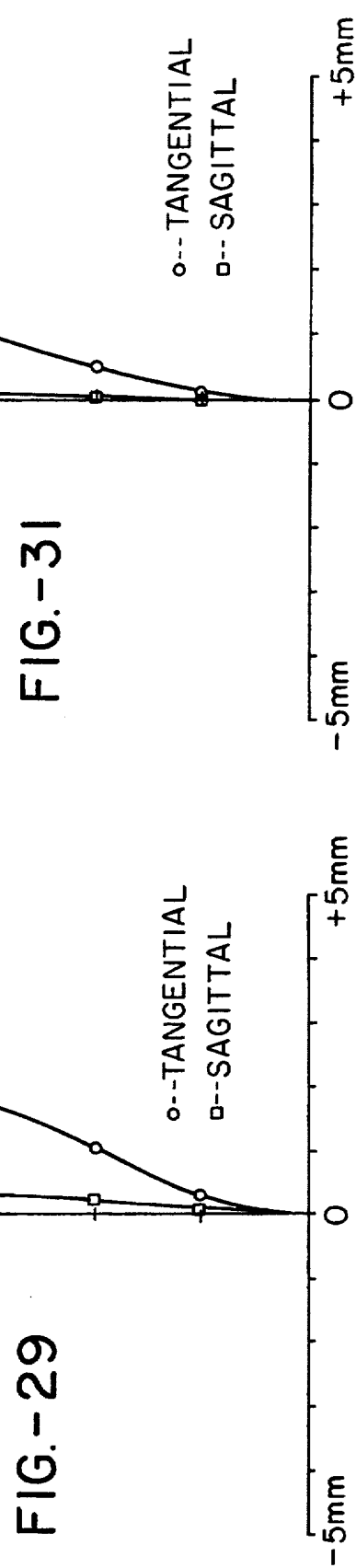
FIG. 31 shows the field curves for the optical system with the adapter lens repositioned as shown in FIG. 30.

In FIG. 30, repositioning of same adapter lens 180 a distance of 9.5 mm from lens 130 results in a significant net system power increase from that of the lens system of FIG. 28, thus providing modified magnification and field characteristics. The resulting net system power is 79 diopters, equal to that of indirect ophthalmoscopy lens 130 itself. Field curves of the system with lens 180 positioned as shown in Fig. 30 are shown in FIG. 31, again indicating good performance of the type previously described. Selective positioning of lens 180 as shown in both FIGS. 28 and 30 may be accomplished by any suitable means associated with adapter housing 186 as previously described, for frictionally or otherwise engaging lens housing 188. For example, frictional engagement of housing 186 with the inner diameter portion 189 of housing 188 will allow sliding of housing 186 relative to housing 188. Alternatives to frictional engagement between housings 186 and 188 are contemplated, such as threaded engagement between the housings may allow selective repositioning of adapter lens 180 relative to lens 130 by screwing or unscrewing the housing 186 relative to housing 188. It is also contemplated within the invention to utilize any other suitable means for enabling repositioning of the adapter lens system relative to the indirect ophthalmoscopy lens system, and means may also be provided for positioning of the adapter lens system in a plurality of specific positions relative to the indirect ophthalmoscopy lens. For example, detents may be provided within lens housing 186 or 188 to precisely position adapter lens 180 in desired positions relative to lens 130. The detents or other means may then allow lens 180 to be easily and selectively moved to provide desired net system power, such as in 5 diopter or other suitable increments for a particular optical system. Thus, the selective movement of lens 180 relative to lens 130 allows the net system power to be adjusted as desired for a particular clinical application. It should be also be recognized that in this particular example, further movement of lens 180 from lens 130 will further increase net system power and cause minification of the observed image is achieved if desired.

In all the designs of the plus and minus powered corneal non-contact adapter lenses, the addition of the adapter lens provides selective modified field and magnification characteristics of the system while simultaneously retaining good retinal and pupil imagery. As the addition of the adapter lens or lenses changes the system power, the indirect ophthalmoscopy lens 130 is used at optical conjugate distances which are different from those for which the lens is used without an adapter lens. This results in a degradation of good imaging properties of the indirect ophthalmoscopy lens itself. Therefore, the adapter lenses are designed to correct for not only their own imaging aberrations, with respect to the retina and the observation pupil, but also to compensate for new aberrations of the indirect ophthalmoscopy lens due to the changed conjugate distances. These goals are achieved by adapter lenses in accordance with the foregoing, through the use of simple spherical or aspherical plano-convex, plano-concave, or other conventional lens designs selectively positioned either in front of or behind the associated indirect ophthalmoscopy lens system.

Although particular power adapter lenses have been shown in the foregoing examples, a wide variety of different power adapter lenses may be used in association with the indirect ophthalmoscopy lens to achieve various magnifications and system characteristics. For example, in the embodiments of a corneal non-contact adapter lens of plano-convex design, good imaging characteristics are provided by an aspherical surface of revolution as the convex surface of the adapter lens when used in association with an indirect ophthalmoscopy lens 130, as described. Used in conjunction with lens 130, a wide range of powers of adapter lenses, providing optimum retinal imagery as well as good pupil imagery, are obtained by forming the aspherical surface of revolution having an eccentricity which is related in a predetermined manner to the apical radius of curvature of the surface. For positive power adapter lenses positioned adjacent to surface 146 of lens 130, it has been found an eccentricity value in the range of 0.12 to 0.22 times the apical radius of curvature provides excellent results regardless of the index of refraction of the lens material. A value of 0.165 times the apical radius provides an optimum results. For negative power plano-concave adapter lenses similarly positioned, an eccentricity value in the range of 0.05 to 0.1 times the radius provides optimum results, again not being dependent upon the index of refraction of the lens material. A value of 0.079 times the apical radius provides optimum results. Based upon the foregoing, the adapter lenses are simply and cost effectively manufactured over a wide range of negative or positive powers based upon the linear relationship between the required conic eccentricity and the apical radius of curvature of the non-plano side of the adapter lens. The result is a simple-to-design series of adapter lenses of both positive and negative power, which provide in conjunction with an indirect ophthalmoscopy lens, a system which is well corrected for both retinal and pupil imagery.

Figure 32:
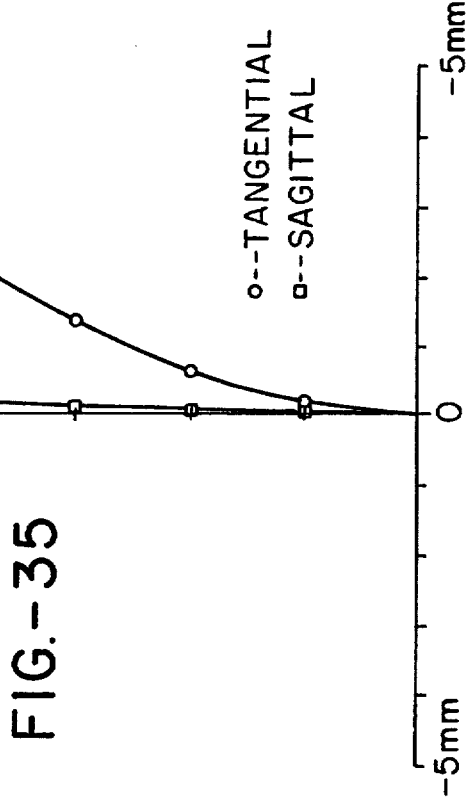
FIG. 32 shows a schematic representation of an alternate embodiment of a lens adapter system in use with an indirect ophthalmoscopy lens, including tangential ray imaging characteristics thereof.

The adapter lenses of the invention may also be of the contact type as shown in FIG. 32. A positive power contact lens 190 includes a first convex surface 192 and a concave surface 194 for contacting the cornea of the eye being examined. The convex surface 192 may be a spherical surface having a radius of curvature of 7.68 mm or may be an aspherical surface as desired. The diameter of the surface is approximately 13.5 mm. The concave surface 194 of the contact adapter lens 190 may be an aspherical surface of revolution having an apical radius of curvature of 7.65 mm and an eccentricity of about 0.425. The lens 190 of this example will have a center thickness of about 5.182 mm. When used in conjunction with an indirect ophthalmoscopy lens 130, the contact adapter lens 190 will change the focal length of the system and therefore the system's net power. In the example of FIG. 32, although the adapter lens 190 has a power of +14 diopters, due to the lens thickness there is caused a substantial increase in net power of the system, totalling approximately 106.5 diopters, providing 29.3 diopters of added power for the system.

Figure 34:
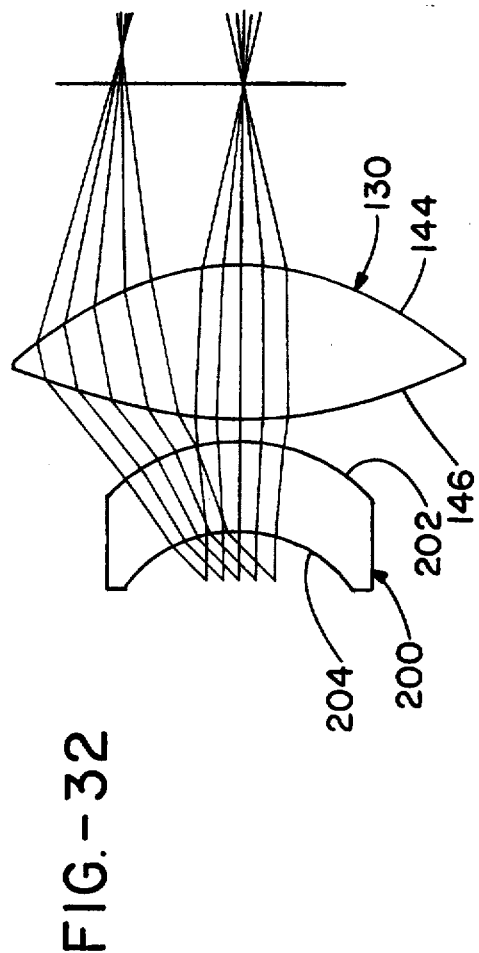
FIG. 34 shows a schematic representation of an alternate embodiment of a lens adapter system in use with an indirect ophthalmoscopy lens, including tangential ray imaging characteristics thereof.
Figure 33:
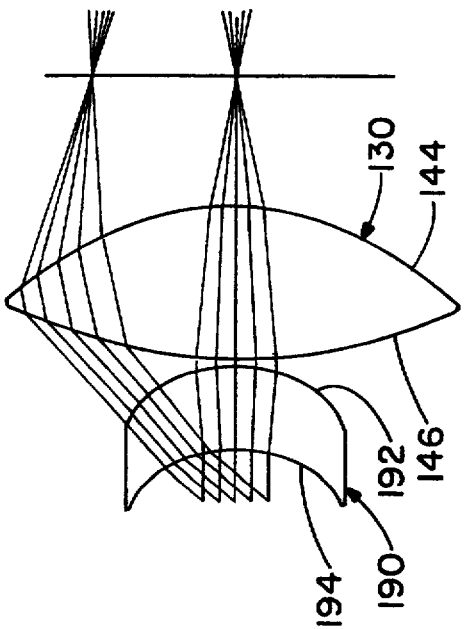
FIG. 33 shows the field curves for a lens adapter system in use with an indirect ophthalmoscopy lens as shown in FIG. 32.
Figure 35:
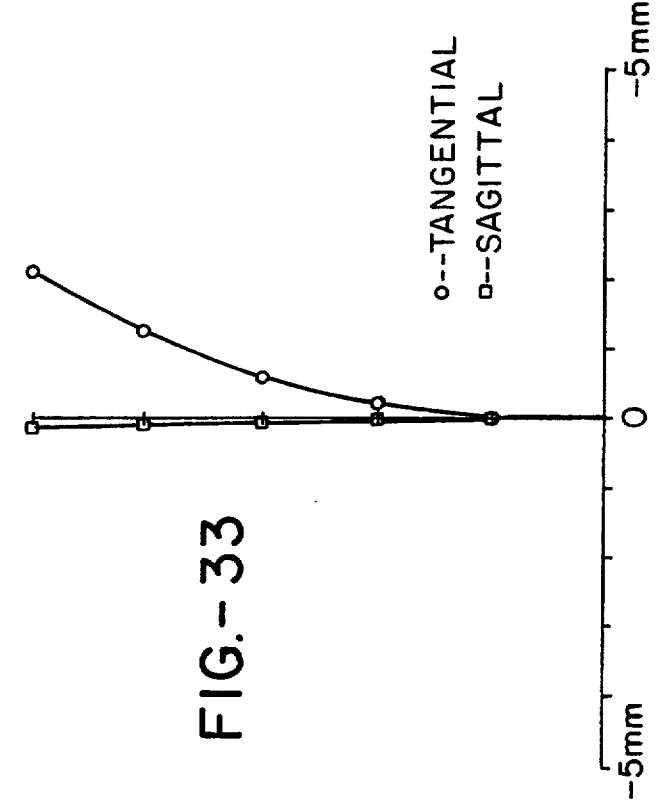
FIG. 35 shows the field curves for a lens adapter system in use with an indirect ophthalmoscopy lens as shown in FIG. 34.

As an alternative, a negative power contact adapter lens 200 may be used in conjunction with an indirect ophthalmoscopy lens 130 as shown in FIG. 34. Lens 200 includes a convex surface 202 and concave surface 204. As an example, the convex surface 202 may be a spherical surface having a radius of curvature of approximately 12 mm, or may be an aspherical surface if desired. The concave surface 204 may be aspherical, having an apical radius of curvature of approximately 7.65 mm and an eccentricity of 0.425. The adapter lens 200 has a power of approximately −14 diopters, and a center thickness of approximately 5.182 mm. Again, the change of the focal length of the system upon addition of the adapter 200 will result in a net power of the system of approximately 88.9 diopters, still providing an increase of net power of about 9.7 diopters over the actual power of the indirect ophthalmoscopy lens 130. To achieve significantly higher magnification, a further lens, such as a minus power plano-concave lens similar to that shown in FIG. 26, may be positioned between the contact lens 200 and indirect ophthalmoscopy lens 130 or on the opposite side of indirect ophthalmoscopy lens 130 from contact lens 200. The field curves for the embodiment as shown in FIGS. 32 and 34 are given in FIGS. 33 and 35 respectively, wherein good retinal imaging as previously described is obtained.

It should be recognized that a wide range of contact lens powers can be used to achieve the desired net power for the combination lens system without significantly changing desirable pupil characteristics of the system. This is due primarily to the meniscus design of the contact element and its proximity to the patient's pupil, and thus the fact that chief rays exiting the cornea and contact lens exit nearly perpendicular to the convex contact lens surface, with little change in the direction of the propagating chief rays. Thus, correct pupil imagery conjugate with the slit lamp exit pupil is maintained, providing for a variety of diagnostic or treatment procedures.

In a further embodiment as shown in FIG. 36, an indirect ophthalmoscopy lens system 210 generally comprises a contact lens 212 and an anterior lens 214. As an example, the contact lens 212 will include a concave surface 216 for positioning on the cornea of the eye being examined, and a convex surface 218. The contact lens 212 may be formed of a plastic material having an index of refraction of 1.491, with surface 216 having an apical radius of curvature of 7.65 and an eccentricity of 0.4, while surface 218 has an apical radius of curvature of 8.8 mm and an eccentricity of 0.37. The lens 214 may be a bi-convex lens having a first convex surface 220 and a second convex surface 222. Surface 220 may have an apical radius of curvature of 19.84 mm and an eccentricity of approximately 1.7, while surface 222 may have an apical radius of curvature of approximately 19.56 mm and an eccentricity of approximately 1.6. The lens 214 may be made of plastic or glass, and in this example is glass having an index of refraction of 1.732. In association with an indirect ophthalmoscopy lens system 210, an adapter lens 224 is positioned anterior to lens 214 to correct for pupil imagery aberrations of the indirect ophthalmoscopy lens system 210. In this embodiment, the system power and imaging characteristics of the indirect ophthalmoscopy lens system 210 remain the same, while pupil imagery of the lens is optimized as desired. The adapter lens 224 includes a first surface 226 and second surface 228, each of which have specialized curves to correct for pupil aberrations of the indirect ophthalmoscopy lens system 210. For example, the surface 226 may be designed as an aspherical surface having an apical radius of curvature of approximately 80.6 mm with a fourth order deformation co-efficient of 3.3804E-05. Similarly, surface 228 may be designed as an aspherical surface having an apical radius of curvature of approximately 20.84 mm with a fourth order deformation co-efficient of 0.00019. It has been found that in order to correct for pupil aberrations of the indirect ophthalmoscopy lens system, a pair of aspherical surfaces similar to that shown in FIG. 36 are required to additionally maintain primary image quality in the resulting optical system. The aspherical surface design preferably will include deformation co-efficients resulting in an inflection point at which the slope of the curved surface reverses. It should be understood that the aspheric curves mentioned above for use with a particular indirect ophthalmoscopy lens system are only representative, and the nature of the surfaces will change according to the particular design of the indirect ophthalmoscopy lens system accordingly. The lens 224 may be made of any suitable optical material, and in this example is a plastic material having an index of refraction of 1.491, and in association with indirect ophthalmoscopy lens system 210 the aspheric adapter will provide correction for pupil aberrations of the indirect lens system 210 while maintaining good primary image quality and leaving the net system power unchanged.

Both non-contact and contact adapter lenses are selectively and easily coupled to the housing associated with an indirect ophthalmoscopy lens system to be positioned adjacent either or both surfaces of the indirect ophthalmoscopy lens as described and when possible, may be used in dual combination with the indirect ophthalmoscopy lens. For example, a minus power non-contact adapter lens, such as a lens 180 may be positioned adjacent to indirect ophthalmoscopy lens surface 144 as described, while a corneal contact lens adapter, such as lens 200 may be coupled to lens housing 132, adjacent to opposite lens surface 146. Thus, a variety of embodiments may be combined and used in conjunction with one another to expand the range and application for both diagnostic laser treatment procedures.

Although preferred embodiments of the invention have been described, it is to be understood that various modifications would be obvious to those skilled in the art, and are embodied within the present invention as defined by the appended claims.

What is claimed is:

1. An indirect ophthalmoscopy lens for use with a slit lamp or other biomicroscope in the examination or laser treatment of a patient's eye, comprising, at least two lens elements having first and second surfaces, each of said first and second surfaces being coaxial and at least one of said surfaces being an aspheric surface of revolution with its magnitude and shape defined by the polynomial expressed as follows:

$$y = (2rx + (e^2-1)x^2)^{\frac{1}{2}} + Ax^F + Bx^G + Cx^H$$

where r equals the apical radius of curvature of the surface, e equals the apical eccentricity of the surface, and co-efficients A, B, and C equal successive terms in the polynomial, and F, G, and H equal exponents in the successive terms respectively, wherein the apical radius of curvature and apical eccentricity of said at least one aspheric surface chosen to satisfy optical correction of image aberrations including curvature, astigmatism, and distortion while concomitantly satisfying optical correction for pupil aberrations in conjunction with the other surfaces of said at least two lens elements, such that the chief rays emerging from a patient's eye which originate at the fundus of the eye and converge at the entrance pupil thereof will be conveyed by said at least two lens elements to a focal area substantially coinciding with the pupil aperture of the objective lens system of the slit lamp or other biomicroscope.

2. The indirect ophthalmoscopy lens of claim 1, wherein,
said at least one aspheric surface is a convex surface having an apical radius of curvature in the range between 10 and 15 mm with an apical eccentricity in the range from 0.5 to 1.5.

3. The indirect ophthalmoscopy lens of claim 1, wherein,
first and second lens elements are provided, with said first lens element being positioned adjacent a patient's eye being examined, and the second lens element positioned anterior to said first lens element, wherein said first and second surfaces of each of said first and second lens elements are the posterior and anterior surfaces respectively, and wherein the said at least one aspheric surface is provided on the anterior surface of said first lens element.

4. The indirect ophthalmoscopy lens of claim 3, wherein,
said posterior surface of said first lens element is a convex spherical surface of revolution.

5. The indirect ophthalmoscopy lens of claim 3, wherein,
said posterior surface of said first lens element is a plano surface.

6. The indirect ophthalmoscopy lens of claim 3, wherein,
said posterior surface of said first lens element is a concave surface.

7. The indirect ophthalmoscopy lens of claim 3, wherein,
said posterior surface of said second lens element is a convex surface.

8. The indirect ophthalmoscopy lens of claim 7, wherein,
said convex posterior surface of said second lens element is a spherical surface.

9. The indirect ophthalmoscopy lens of claim 7, wherein,
said convex posterior surface of said second lens element is an aspherical surface.

10. The indirect ophthalmoscopy lens of claim 3, wherein, said posterior surface of said second lens is a planar surface.

11. The indirect ophthalmoscopy lens of claim 3, wherein,
said posterior surface of said second lens is a concave surface.

12. The indirect ophthalmoscopy lens of claim 3, wherein,
said anterior surface of said second lens element is a convex surface.

13. The indirect ophthalmoscopy lens of claim 12, wherein,
said convex anterior surface of said second lens element is a spherical surface of revolution.

14. The indirect ophthalmoscopy lens of claim 12, wherein,
said convex anterior surface of said second lens element is an aspherical surface of revolution.

15. The indirect ophthalmoscopy lens of claim 3, wherein, said anterior surface of said second lens element is a planar surface.

16. The indirect ophthalmoscopy lens of claim 3, wherein, said anterior surface of said second lens element is a concave surface.

17. The indirect ophthalmoscopy lens of claim 1, wherein,
a contact lens is provided in addition to said at least two lens elements, said contact lens having a posterior surface adapted to be placed upon the cornea of a patient's eye to be examined and an anterior surface in spaced relationship to said at least two lens elements.

18. An indirect ophthalmoscopy lens for use with a slit lamp or other biomicroscope in the examination or laser treatment of a patient's eye, comprising,
a contact lens element and at least one additional lens element, said contact lens element including a concave posterior surface and an anterior surface, said posterior surface adapted to be positioned on the cornea of a patient's eye to be examined, said at least one additional lens element having first and second surfaces, with at least one of said first or second surfaces being a convex aspheric surface of revolution with its magnitude and shape defined by the polynomial expressed as follows:

$$y = (2rx + (e^2 - 1)x^2)^{\frac{1}{2}} + Ax^F + Bx^G + Cx^H$$

where r equals the apical radius of curvature of the surface, e equals the apical eccentricity of the surface, and co-efficients A, B, and C equal successive terms in the polynomial, and F, G, and H equal exponents in the successive terms respectively, wherein the apical radius of curvature and apical eccentricity of said at least one aspheric surface chosen to satisfy optical correction of image aberrations including curvature, astigmatism, and distortion while concomitantly satisfying optical correction for pupil aberrations in conjunction with the other of said surfaces of said at least one additional lens element and said contact lens, such that the chief rays emerging from a patient's eye which originate at the fundus of the eye and converge at the entrance pupil thereof will be conveyed by said at least one additional lens to a focal area substantially coinciding with the pupil aperture of the objective lens system of the slit lamp or other biomicroscope.

19. An adapter lens for use with an indirect ophthalmoscopy lens in the examination or laser treatment of a patient's eye, comprising:
at least one adapter lens element including first and second surfaces, said at least one adapter lens element positioned within an adapter housing,
said adapter housing including means for selectively attaching said adapter housing to a housing associated with an indirect ophthalmoscopy lens system, wherein upon attachment of said adapter housing to the housing of an indirect ophthalmoscopy lens, the said at least one adapter lens element is positioned in predetermined relation to a lens of said indirect ophthalmoscopy lens system, wherein said at least one adapter lens element will modify the magnification or imaging characteristics of the indirect ophthalmoscopy lens system in a selective and predetermined manner.

20. The adapter lens system of claim 19, wherein,
said at least one adapter lens element is a plano-convex lens element positioned between said patient's eye and the indirect ophthalmoscopy lens system.

21. The adapter lens system of claim 19, wherein,
said convex surface of said at least one adapter lens element is an aspheric surface of revolution having a predetermined apical radius of curvature, and an eccentricity in the range of 0.12 to 0.22 times said apical radius of curvature.

22. The adapter of lens system of claim 19, wherein,
said at least one adapter lens element is a meniscus lens positioned between said patient's eye and said indirect ophthalmoscopy lens system.

23. The adapter lens system of claim 19, wherein,
said at least one adapter lens element is a plano-concave lens element positioned between said patient's eye and said indirect ophthalmoscopy lens system.

24. The adapter lens system of claim 19, wherein,
said concave surface of said at least one adapter lens element is an aspheric surface of revolution having a predetermined apical radius of curvature, and an eccentricity in the range of 0.05 to 0.10 times said apical radius of curvature.

25. The adapter lens system of claim 19, wherein,
said at least one adapter lens element is a plus powered lens which when selectively positioned relative to said indirect ophthalmoscopy lens system will increase the net power of the lens system.

26. The adapter lens system of claim 19, wherein,
said at least one adapter lens element is a negative powered lens which when used in combination with said indirect ophthalmoscopy lens system will result in a predetermined net power for the optical system.

27. The adapter lens system of claim 19, wherein,
said at least one adapter lens element is a non-contact lens.

28. The adapter lens system of claim 19, wherein,
said at least one adapter lens element is contact lens having a posterior surface to be positioned on the cornea of said patient's eye.

29. The adapter lens system of claim 19, wherein,
said means for attachment is an outer surface on said adapter lens housing which is frictionally engageable on an interior surface of said housing of the indirect ophthalmoscopy lens system.

30. The adapter lens system of claim 29, wherein, said outer surface includes resilient means associated therewith for frictionally engaging said interior surface of said housing.

31. The adapter lens system of claim 30, wherein,
said resilient means is an o-ring positioned on said outer surface which frictionally engages said interior surface and provides a seal between said adapter lens housing and said housing of said indirect ophthalmoscopy lens system.

32. The adapter lens system of claim 19, wherein,
said at least one adapter lens element has at least one aspherical surface with its magnitude and shape defined by the polynomial expressed as follows:

$$y = (2rx + (e^2 - 1)x^2)^{\frac{1}{2}} + Ax^F + Bx^G + Cx^H$$

where r equals the apical radius of curvature of the surface, e equals the apical eccentricity of the surface, and co-efficients A, B, and C equal successive terms in the polynomial, and F, G, and H equal exponents in the successive terms respectively, wherein the apical radius of curvature and apical eccentricity of said at least one aspheric surface are chosen to satisfy optical correction of image aberrations including curvature, astigmatism, and distortion while concomitantly satisfying optical correction for pupil aberrations, such that the chief rays emerging from a patient's eye which originate at the fundus of the eye and converge at the entrance pupil thereof will be conveyed through said adapter lens system in combination with an indirect ophthalmoscopy lens system to a focal area substantially coinciding with the pupil aperture of the objective lens system of the slit lamp or other biomicroscope.

33. The adapter lens system of claim 19, wherein
said at least one adapter lens element is selectively movable along the optical axis of said indirect ophthalmoscopy lens system to modify the net power of the optical system.

34. The adapter lens system of claim 19, wherein
said at least one adapter lens element corrects for pupil aberration of said indirect ophthalmoscopy lens system, such that when used in conjunction with said indirect ophthalmoscopy lens system, chief light rays emerging from a patient's eye which originate at the fundus of the eye and converge at the entrance pupil thereof will be conveyed to a focal area substantially coinciding with the pupil aperture of the objective lens system of the slit lamp or other biomicroscope.

* * * * *